US007132261B2

(12) United States Patent
Kuiper et al.

(10) Patent No.: US 7,132,261 B2
(45) Date of Patent: *Nov. 7, 2006

(54) ORPHAN RECEPTOR

(75) Inventors: Georg Kuiper, Huddinge (SE); Eva L. K. Enmark, Tullinge (SE); Jan-Ake Gustafsson, Stockholm (SE)

(73) Assignee: Karo Bio AB, Huddinge (SE)

( * ) Notice: Subject to any disclaimer, the term of this patent is extended or adjusted under 35 U.S.C. 154(b) by 169 days.

This patent is subject to a terminal disclaimer.

(21) Appl. No.: 10/278,481

(22) Filed: Oct. 23, 2002

(65) Prior Publication Data

US 2003/0113803 A1 Jun. 19, 2003

Related U.S. Application Data

(63) Continuation of application No. 10/083,807, filed on Feb. 27, 2002, now abandoned, which is a continuation of application No. 09/333,057, filed on Jun. 14, 1999, now abandoned, which is a continuation of application No. 08/836,620, filed as application No. PCT/EP96/03933 on Sep. 9, 1996, now Pat. No. 5,958,710.

(30) Foreign Application Priority Data

| Sep. 8, 1995 | (GB) | ................................ 9518272.1 |
| Mar. 15, 1996 | (GB) | ................................ 9605550.4 |
| Apr. 11, 1996 | (GB) | ................................ 9607532.0 |
| May 8, 1996 | (GB) | ................................ 9609576.5 |

(51) Int. Cl.
*C12N 15/12* (2006.01)
*C07K 14/705* (2006.01)
*C12P 21/06* (2006.01)

(52) U.S. Cl. ................. 435/69.1; 536/23.5; 435/320.1; 435/325; 530/350

(58) Field of Classification Search ............... 536/23.5; 530/350; 435/7.21, 6, 69.1, 320.1, 325
See application file for complete search history.

(56) References Cited

U.S. PATENT DOCUMENTS

| 5,071,773 A | 12/1991 | Evans et al. ................. 436/501 |
| 5,217,867 A | 6/1993 | Evans et al. .................. 435/7.1 |
| 5,262,300 A | 11/1993 | Evans et al. .................... 435/6 |
| 5,298,429 A | 3/1994 | Evans et al. ................. 436/501 |
| 5,310,662 A | 5/1994 | Evans et al. ................. 435/69.1 |
| 5,312,732 A | 5/1994 | Evans et al. ................. 435/69.1 |
| 5,438,126 A | 8/1995 | DeGroot et al. ............. 536/23.5 |
| 5,534,418 A | 7/1996 | Evans et al. ................. 435/69.1 |
| 5,597,693 A | 1/1997 | Evans et al. .................... 435/6 |
| 5,597,705 A | 1/1997 | Evans et al. ................. 435/69.1 |
| 5,599,904 A | 2/1997 | Evans et al. ................. 530/350 |
| 5,602,009 A | 2/1997 | Evans et al. ................. 435/69.7 |
| 5,639,616 A | 6/1997 | Liao et al. .................... 435/7.1 |
| 5,712,372 A | 1/1998 | DeGroot et al. ........ 530/388.22 |
| 6,680,368 B1 * | 1/2004 | Mosselman et al. ........ 530/350 |
| 6,713,270 B1 * | 3/2004 | Mosselman et al. ......... 435/7.8 |

FOREIGN PATENT DOCUMENTS

| EP | 0 733 705 A1 | 9/1996 |
| EP | 0 798 378 A | 10/1997 |

OTHER PUBLICATIONS

Toresani et al., "Partial Purification And Characterization Of Nuclear Triiodothyronine Binding Proteins" *Biochemical And Biophysical Research Communications*, vol. 81, No. 1, 1978.
Mosselman et al., "ERβ: identification and characterization of a novel human estrogen receptor", *FEBS Letters* 392, 1996, pp. 49-53.
Vennstrom et al., "Isolation and Characterization of Chicken DNA Homologous to the Two Putative Oncogenes of Avian Erythroblastosis Virus", *Cell*, vol. 28, Jan. 1982, pp. 135-143.
Debuire et al., Sequencing the erbA Gene of Avian Erythroblastosis Virus Reveals a New Type of Oncogene, *Science*, vol. 224, Jun. 1984.
Weinberger et al., "Domain structure of human glucocorticoid receptor and its relationship to the v-erb-A oncogene product", *Nature*, vol. 318, Dec. 1985.
Green et al . . . , Human oestrogen receptor cDNA: sequence, expression and homology to v-erb-A, *Nature*, vol. 320, Mar. 1986.
Greene et al., "Sequence and Expression of Human Estrogen Receptor Complementary DNA", *Science*, vol. 231, Mar. 1986.
Bishop, "Oncogenes as hormone receptors", *Nature*, vol. 321, May 1986.
Latham et al., "Solubilized Nuclear 'Receptors' for Thyroid Hormones", Journal of Biological Chemistry, vol. 251, No. 23, Dec. 1976, pp. 7388-7397.
Silva et al., "Partial Purification of Triiodothyronine Receptor from Rat Liver Nuclei", *Journal of Biological Chemistry*, vol. 252, No. 19, Oct. 1977, pp. 6799-6805.
Nikodem et al., "Affinity labeling of rat liver thyroid hormone nuclear receptor", *Proc. Natl. Acad. Sci. USA*, vol. 77, No. 12, Dec. 1980, pp. 7064-7068.
Aprilett et al., "Affinity Chromatography of Thyroid Hormone Receptors", *Journal of Biological Chemistry*, vol. 256, No. 23, Dec. 1981, pp. 12094-12101.

(Continued)

*Primary Examiner*—Marianne P. Allen
(74) *Attorney, Agent, or Firm*—Todd E. Garabedian; Wiggin and Dana LLP

(57) ABSTRACT

This invention relates to a novel estrogen receptor-related nuclear receptor, hereinafter termed "ERβ" having the amino acid sequence of FIG. 1, 13A or 14A or substantially the same amino acid sequence as the amino acid sequence shown in FIG. 1, 13A or 13B or an amino acid sequence functionally similar to that sequence. The invention also relates to DNA sequences encoding the receptor. The receptor may be useful in isolating molecules for the treatment of disorders such as prostate cancer, benign prostatic hyperplasia, osteoporosis or cardiovascular disorders and in the testing of substances for estrogenic and other hormonal effects.

13 Claims, 17 Drawing Sheets

OTHER PUBLICATIONS

Casanova et al., "5'-Flanking DNA of the Rat Growth Hormone Gene Mediates Regulated Expression by Thyroid Hormone", *Journal of Biological Chemistry*, vol. 260, No. 21, Sep. 1985, pp. 11744-11748.

Cattini et al., "The Human Growth Hormone Gene Is Negatively Regulated by Triiodothyronine When Transferred into Rat Pituitary Tumor Cells", *Journal of Biological Chemistry*, vol. 261, No. 28, Oct. 1986, pp. 13367-13372.

Spurr et al., "Chromosomal localisation of the human homologues to the oncogenes erbA and B", *EMBO Journal*, vol. 3, No. 1, 1984, pp. 159-163.

Jhanwar et al., "Germ-Line Chromosomal Localization of Human C-Erb-A Oncogene", Somatic Cell and Molecular Genetics, vol. 11, No. 1, 1985, pp. 99-102.

Zabel et al., "Cellular homologs of the avian erythroblastosis virus erb-A and erb-B genes are syntenic in mouse but asyntenic in man", *Proc. Natl. Acad. Sci. USA*, vol. 81, Aug. 1984, pp. 4874-4878.

Pascual et al., "Photoaffinity Labeling of Thyroid Hormone Nuclear Receptors in Intact Cells", *Journal of Biological Chemistry*, vol. 257, No. 16, Aug. 1982, pp. 9640-9647.

Casanova et al., "Photoaffinity Labeling of Thyroid Hormone Nuclear Receptors", *Journal of Biological Chemistry*, vol. 289, No. 19, Oct. 1984, pp. 12084-12091.

Hitpab et al., "An Estrogen-Responsive Element Derived from the 5' Flanking Region of the Xenopus Vitellogenin A2 Gene Functions in Transfected Human Cells", *Cell*, vol. 46, Sep. 1986.

Bolger et al., "Molecular Interactions between Thyroid Hormone Analogs and the Rat Liver Nuclear Receptor", *Journal of Biological Chemistry*, vol. 255, No. 21, Nov. 1980, pp. 10271-10278.

Weinberger et al., "The c-erb gene encodes a thyroid hormone receptor", *Nature*, vol. 324, Dec. 1986.

Sap et al., "The c-erb A protein is a high-affinity receptor for thyroid hormone", *Nature*, vol. 324, Dec. 1986.

Thompson et al., "Identification of a Novel Thyroid Hormone Receptor Expressed in the Mammalian Central Nervous System", *Science*, vol. 327, Sep. 1987.

Damm et al., "A single point mutation in erbA restores the erythroid transforming potential of a mutant avian erythroblastosis virus (AEV) defective in both erbA and erbB oncogenes", *EMBO Journal*, vol. 6, No. 2, 1987, pp. 375-382.

Ichikawa et al., "Purification and characterization of rat liver nuclear thyroid hormone receptors", *Proc. Natl. Acad. Sci. USA*, vol. 84, May 1987, pp. 3420-3424.

Koenig et al., "Thyroid hormone receptor binds to a site in the rat growth hormone", *Proc. Natl. Acad. Sci. USA*, vol. 84, Aug. 1987, pp. 5670-5674.

Wight et al., "Discrete Positive and Negative Thyroid Hormone-responsive Transcription Regulatory Elements of the Rat Growth Hormone Gene", *Journal of Biological Chemistry*, vol. 262, Apr. 1987.

West et al., "Interaction of a Tissue-Specific Factor with an Essential Rat Growth Hormone Gene Promoter Element", *Molecular and Cellular Biology*, vol. 7, No. 3, Mar. 1987, pp. 1193-1197.

Druege et al., "Introduction of estrogen-responsiveness into mammalian cell lines", *Nucleic Acids Research*, vol. 14, No. 23, 1986.

Underwood et al., "A thyromimetic that drecreases plasma cholesterol levels without increasing cardiac activity", *Nature*, vol. 324, Dec. 1986.

Latham et al., "Interaction of Amiodarone and Desethylamiodarone With Solubilized Nuclear Thyroid Hormone Receptors", *JACC*, vol. 9, No. 4, 1987, pp. 872-876.

Giguere et al., "Functional Domains of the Human Glucocorticoid Receptor", *Cell*, vol. 46, Aug. 1986, pp. 646-652.

Weinberger et al., "Human Steroid Receptors and erbA Proto-oncogene Products: Members of a New Superfamily of Enhancer Binding Proteins", appearing at Cold Spring Harbor Symposia on Quantitative Biology, vol. LI, 1986.

Angier, N., "New Respect for Estrogen's Influence", *The New York Times*, Jun. 24, 1997.

Pennisi, E., "Differing Roles Found for Estrogen's Two Receptors", *Science*, vol. 277, Sep. 1997, p. 1439.

Parker, M., "Nuclear receptor superfamily reunion", *Trends in Genetics*, vol. 12, No. 7, Jul. 1996. pp. 277-278.

"Novel Estrogen Receptor Discovered", *Environmental Health Perspectives*, vol. 104, No. 12, Dec. 1996, pp. 1273-1274.

Katzenellenbogen, B. et al., "A New Actor in the Estrogen Receptor Drama ; Enter ER-β", *Endocrinology 186*: 861-862 (1997).

Enmark, E. et al., "Human Estrogen Receptor β-Gene Structure, Chromonsomal Localization, and Expression Pattern", *Journal of Clinical Endocrinology and Metabolism*, vol. 82, No. 12, 1997.

* cited by examiner

FIG. 1

```
ggaattcCGGGGGAGCTGGCCCAGGGGGAGCGGCTGGTGCTGCCACTGGCATCCCTAGGC    60
ACCCAGGTCTGCAATAAAGTCTGGCAGCCACTGCATGGCTGAGCGACAACCAGTGGCTGG   120
GAGTCCGGCTCTGTGGCTGAGGAAAGCACCTGTCTGCATTTAGAGAATGCAAAATAGAGA   180
ATGTTTACCTGCCAGTCATTACATCTGAGTCCCATGAGTCTCTGAGAACATAATGTCCAT   240
CTGTACCTCTTCTCACAAGGAGTTTTCTCAGCTGCGACCCTCTGAAGACATGGAGATCAA   300
AAACTCACCGTCGAGCCTTAGTTCCCTGCTTCCTATAACTGTAGCCAGTCATCCTACCC    360
CTGGAGCACGGCCCCATCTACATCCCTTCCTCCTACGTAGACAACCGCCATGAGTATTCA   420
GCTATGACATTCTACAGTCCTGCTGTGATGAACTACAGTGTTCCCGGCAGCACCAGTAAC   480
        M  T  F  Y  S  P  A  V  M  N  Y  S  V  P  G  S  T  S  N
CTGGACGGTGGGCCTGTCCGACTGAGCACAAGCCCAAATGTGCTATGGCCAACTTCTGGG   540
 L  D  G  G  P  V  R  L  S  T  S  P  N  V  L  W  P  T  S  G
CACCTGTCTCCTTTAGCGACCCATTGCCAATCATCGCTCCTCTATGCAGAACCTCAAAAG   600
 H  L  S  P  L  A  T  H  C  Q  S  S  L  L  Y  A  E  P  Q  K
AGTCCTTGGTGTGAAGCAAGATCACTAGAGCACACCTTACCTGTAAACAGAGAGACACTG   660
 S  P  W  C  E  A  R  S  L  E  H  T  L  P  V  N  R  E  T  L
AAGAGGAAGCTTAGTGGGAGCAGTTGTGCCAGCCCTGTTACTAGTCCAAACGCAAAGAGG   720
 K  R  K  L  S  G  S  S  C  A  S  P  V  T  S  P  N  A  K  R
GATGCTCACTTCTGCCCCGTCTGCAGCGATTATGCATCTGGGTATCATTACGGCGTTTGG   780
 D  A  H  F  C  P  V  C  S  D  Y  A  S  G  Y  H  Y  G  V  W
TCATGTGAAGGATGTAAGGCCTTTTTTAAAAGAAGCATTCAAGGACATAATGATTATATC   840
 S  C  E  G  C  K  A  F  F  K  R  S  I  Q  G  H  N  D  Y  I
TGTCCAGCCACGAATCAGTGTACCATAGACAAGAACCGGCGTAAAAGCTGCCAGGCCTGC   900
 C  P  A  T  N  Q  C  T  I  D  K  N  R  R  K  S  C  Q  A  C
CGACTTCGCAAGTGTTATGAAGTAGGAATGGTCAAGTGTGGATCCAGGAGAGAACGGTGT   960
 R  L  R  K  C  Y  E  V  G  M  V  K  C  G  S  R  R  E  R  C
GGGTACCGTATAGTGCGGAGGCAGAGAAGTTCTAGCGAGCAGGTACACTGCCTGAGCAAA  1020
 G  Y  R  I  V  R  R  Q  R  S  S  S  E  Q  V  H  C  L  S  K
GCCAAGAGAAACGGTGGGCATGCACCCCGGGTGAAGGAGCTACTGCTGAGCACCTTGAGT  1080
 A  K  R  N  G  G  H  A  P  R  V  K  E  L  L  L  S  T  L  S
CCAGAGCAACTGGTGCTCACCCTCCTGGAAGCTGAACCACCCAATGTGCTGGTGAGCCGT  1140
 P  E  Q  L  V  L  T  L  L  E  A  P  P  N  V  L  V  S  R
CCCAGCATGCCCTTCACCGAGGCCTCCATGATGATGTCCCTCACTAAGCTGGCGGACAAG  1200
 P  S  M  P  F  T  E  A  S  M  M  M  S  L  T  K  L  A  D  K
GAACTGGTGCACATGATTGGCTGGGCCAAGAAAATCCCTGGCTTTGTGGAGCTCAGCCTG  1260
 E  L  V  H  M  I  G  W  A  K  K  I  P  G  F  V  E  L  S  L
TTGGACCAAGTCCGGCTCTTAGAAAGCTGCTGGATGGAGGTGCTAATGGTGGGACTGATG  1320
 L  D  Q  V  R  L  L  E  S  C  W  M  E  V  L  M  V  G  L  M
TGGCGCTCCATCGACCACCCCGGCAAGCTCATTTTCGCTCCCGACCTCGTTCTGGACAGG  1380
 W  R  S  I  D  H  P  G  K  L  I  F  A  P  D  L  V  L  D  R
GATGAGGGGAAGTGCGTAGAAGGGATTCTGGAAATCTTTGACATGCTCCTGGCGACGACG  1440
 D  E  G  K  C  V  E  G  I  L  E  I  F  D  M  L  L  A  T  T
TCAAGGTTCCGTGAGTTAAAACTCCAGCACAAGGAGTATCTCTGTGTGAAGGCCATGATC  1500
 S  R  F  R  E  L  K  L  Q  H  K  E  Y  L  C  V  K  A  M  I
CTCCTCAACTCCAGTATGTACCCCTTGGCTTCTGCAAACCAGGAGGCAGAAAGTAGCCGG  1560
 L  L  N  S  S  M  Y  P  L  A  S  A  N  Q  E  A  E  S  S  R
AAGCTGACACACCTACTGAACGCGGTGACAGATGCCCTGGTCTGGGTGATTGCAAGAGT   1620
 K  L  T  H  L  L  N  A  V  T  D  A  L  V  W  V  I  A  K  S
GGTATCTCCTCCCAGCAGCAGTCAGTCCGACTGGCCAACCTCCTGATGCTTCTTTCTCAC  1680
 G  I  S  S  Q  Q  Q  S  V  R  L  A  N  L  L  M  L  L  S  H
GTCAGGCACATCAGTAACAAGGGCATGGAACATCTGCTCAGCATGAAGTGCAAAAATGTG  1740
 V  R  H  I  S  N  K  G  M  E  H  L  L  S  M  K  C  K  N  V
GTCCCGGTGTATGACCTGCTGCTGGAGATGCTGAATGCTCACACGCTTCGAGGGTACAAG  1800
 V  P  V  Y  D  L  L  L  E  M  L  N  A  H  T  L  R  G  Y  K
TCCTCAATCTCGGGGTCTGAGTGCAGCTCAACAGAGGACAGTAAGAACAAAGAGAGCTCC  1860
 S  S  I  S  G  S  E  C  S  S  T  E  D  S  K  N  K  E  S  S
CAGAACCTACAGTCTCAGTGATGGCCAGGCCTGAGGCGGACAGACTACAGAGATGGTCAA  1920
 Q  N  L  Q  S  Q  *
AAGTGGAACATGTACCCTAGCATCTGGGGGTTCCTCTTAGGGCTGCCTTGGTTACGCACC  1980
CCTTACCCACACTGCACTTCCCAGGAGTCAGGGTGGTTGTGTGGCGGTGTTCCTCATACC  2040
AGGATGTACCACCGAATGCCAAGTTCTAACTTGTATAGCCTTGAAGGCTCTCGGTGTACT  2100
TACTTTCTGTCTCCTTGCCCACTTGGAAACATCTGAAAGGTTCTGGAACTAAAGGTCAAA  2160
GTCTGATTTGGAAGGATTGTCCTTAGTCAGGAAAAGGAATATGGCATGTGACACAGCTAT  2220
AAGAAATGGACTGTAGGACTGTGTGGCCATAAAATCAACCTTTGGATGCGTCTTCTAGA   2280
CCACTTGATTGTAGGATTGAAAACCACATTGACAATCAGCTCATTTCGCATTCCTGCCTC  2340
ACGGGTCTGTGAGGACTCATTAATGTCATGGGTTATTCTATCAAAGACCAGAAAGATAGT  2400
GCAAGCTTAGATGTACCTTGTTCCTCCTCCCAGACCCTTGGGTTACATCCTTAGAGCCTG  2460
CTTATTTGGTCTGTCTGAATGTGGTCATTGTCATGGGTTAAGATTTAAATCTCTTTGTAA  2520
TATTGGCTTCCTTGAAGCTATGTCATCTTTCTCTCTCTCCCGgaattc              2568
```

FIG. 2A
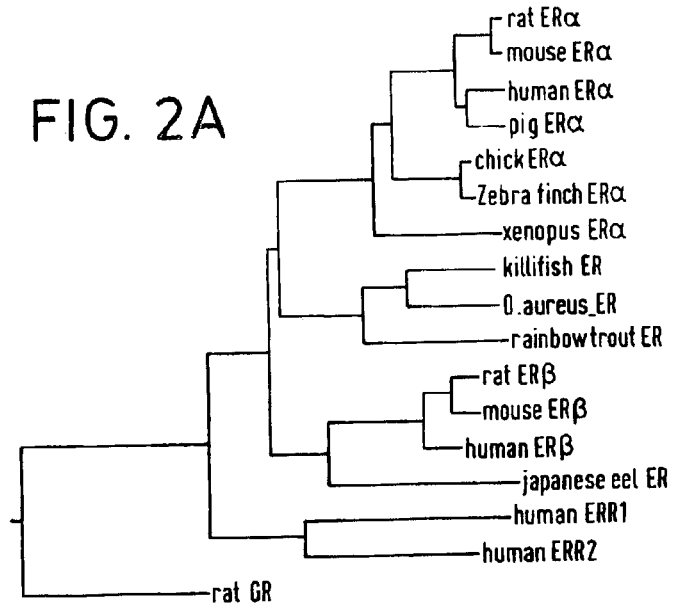
FIG. 2B  ALIGNMENT OF ERβ TO OTHER ESTROGEN RECEPTORS
| A/B | D/E D | D | E/F | rat ERβ |
 human ERβ
 mouse ERβ
 rat ERα
 human ERα
 human ERR1
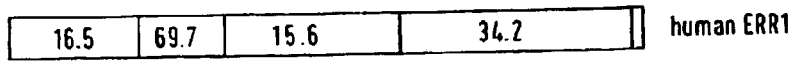 human ERR2

FIG. 2C

DNA-binding domain

| | C P V C S D Y A S G Y H Y G V W S C E G C K A F F K R S I Q G H N D Y I C P A T N Q C T I D K N R R K S C Q A C R L R K C Y E V G M | |
|---|---|---|
| | . . . . . . . . . . . . . . . . . . . . . . . . . . . . . . . . . . . . . . . . . . . . . . . . . . . . . . . . . . . . . . . . . . | ERβ rat |
| | A . N . . . . . . . . . . . . . . . . . . . . . . . . . . . . . . . . . M . . . . . . . . . . . . . . . . . . . . . . . . . . . . . | ER rat |
| | A . N . . . . . . . . . . . . . . . . . . . . . . . . . . . . . . . . . M . . . . . . . . . . . . . . . . . . . . . . . . . . . . . | ER mouse |
| | A . N . . . . . . . . . . . . . . . . . . . . . . . . . . . . . . . . . M . . . . . . . . . . . . . . . . . . . . . . . . . . . . . | ER human |

FIG. 2D

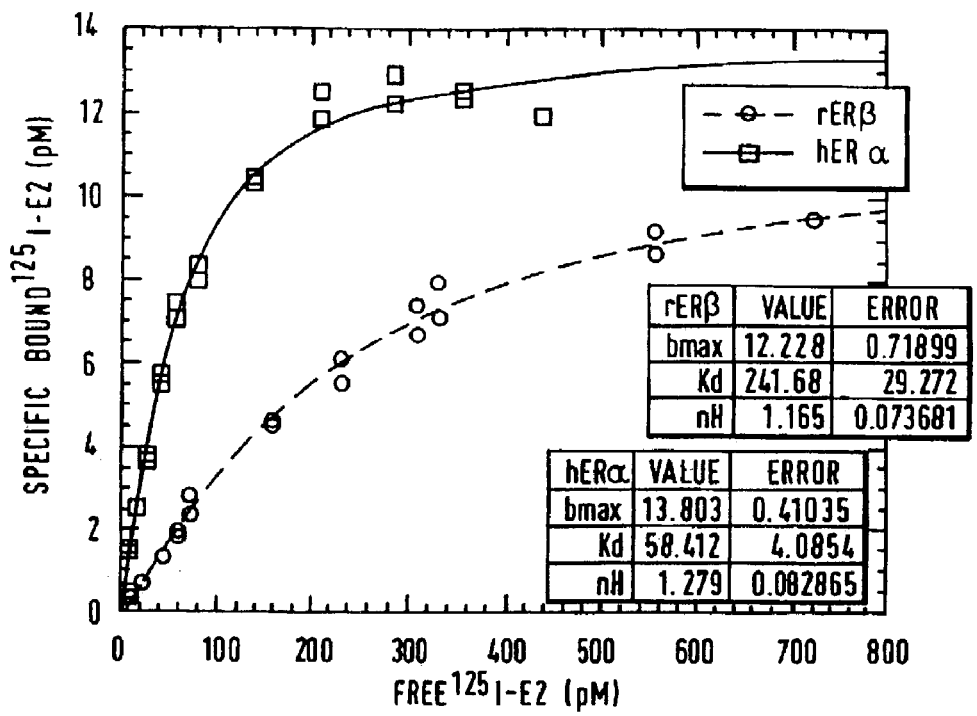
FIG. 10A HILL PLOT COMPARING hERα AND rERβ.
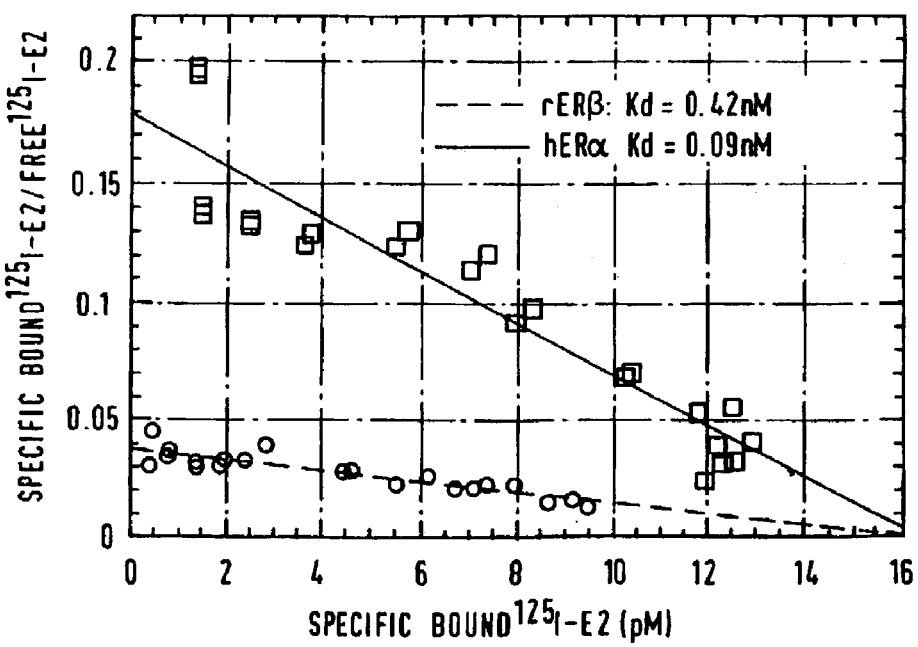
FIG. 10B SCATCHARD PLOT COMPARING hERα AND rERβ.

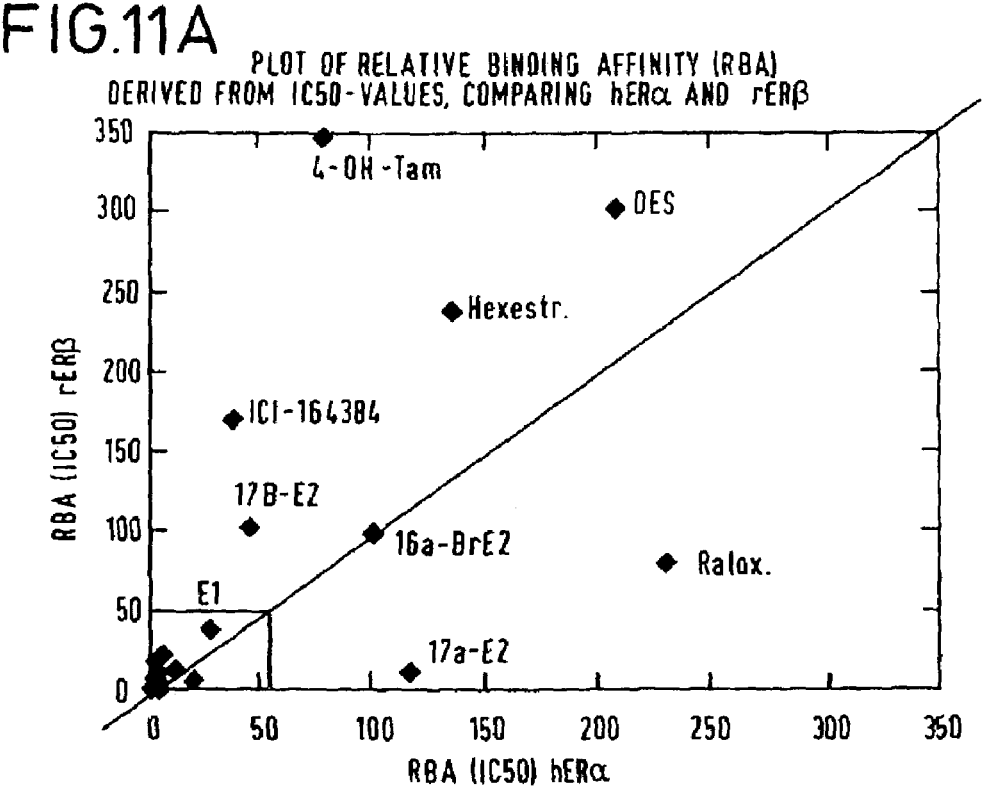
FIG.11A PLOT OF RELATIVE BINDING AFFINITY (RBA) DERIVED FROM IC50-VALUES, COMPARING hERα AND rERβ
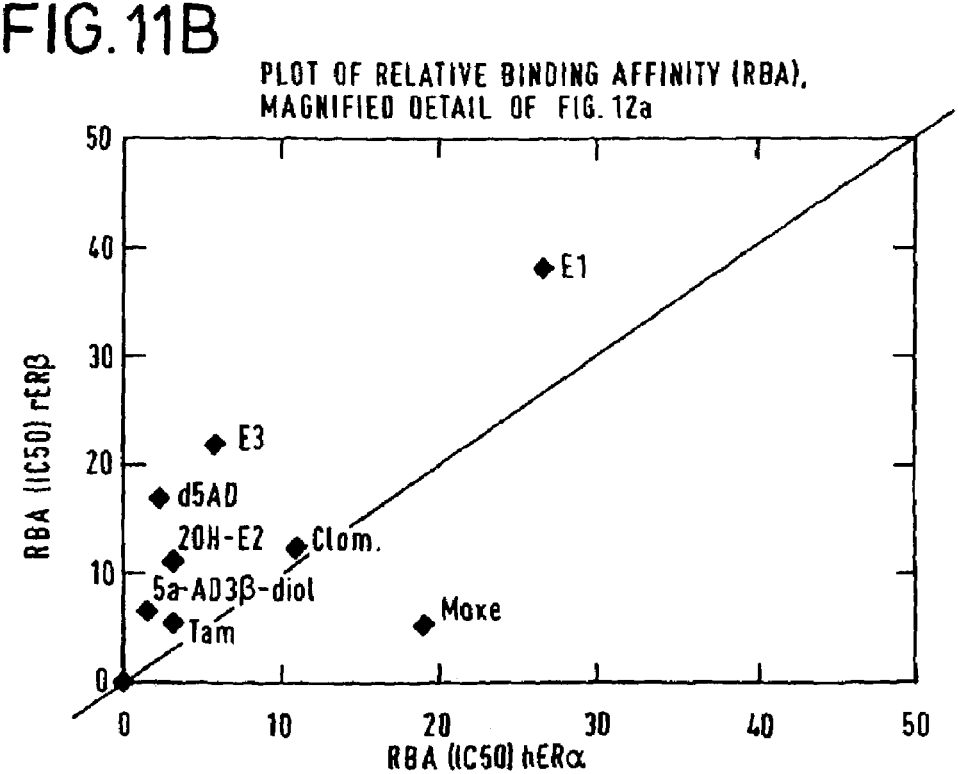
FIG.11B PLOT OF RELATIVE BINDING AFFINITY (RBA), MAGNIFIED DETAIL OF FIG.12a

FIG. 12

```
  1  MTFYSPAVMN  YSIPSNVTNL  EGGPGRQTTS  PNVLWPTPGH  LSPLVVHRQL
 51  SHLYAEPQKS  PWCEARSLEH  TLPVNRETLK  RKVSGNRCAS  PVTGPGSKRD
101  AHFCAVCSDY  ASGYHYGVWS  CEGCKAFFKR  SIQGHNDYIC  PATNQCTIDK
151  NRRKSCQACR  LRKCYEVGMV  KCGSRRERCG  YRLVRRQRSA  DEQLHCAGKA
201  KRSGGHAPRV  RELLLDALSP  EQLVLTLLEA  EPPHVLISRP  SAPFTEASMM
251  MSLTKLADKE  LVHMISWAKK  IPGFVELSLF  DQVRLLESCW  MEVLMMGLMW
301  RSIDHPGKLI  FAPDLVLDRD  EGKCVEGILE  IFDMLLATTS  RFRELKLQHK
351  EYLCVKAMIL  LNSSMYPLVT  ATQDADSSRK  LAHLLNAVTD  ALVWVIAKSG
401  ISSQQQSMRL  ANLLMLLSHV  RHASNKGMEH  LLNMKCKNVV  PVYDLLLEML
451  NAHVLRGCKS  SITGSECSPA  EDSKSKEGSQ  NLQSQ*
```

FIG. 13A

```
MAFYSPAVMNYSVPSSTGNLEGGPVRQTASPNVLWPTSGH  40
LSPLATHCQSSLLYAEPQKSPWCEARSLEHTLPVNRETLK  80
RKLGGSGCASPVTSPSTKRDAHFCAVCSDYASGYHYGVWS  120
CEGCKAFFKRSIQGHNDYICPATNQCTIDKNRRKNCQACR  160
LRKCYEVGMVKCGSRRERCGYRIVRRQRSASEQVHCLNKA  200
KRTSGHTPRVKELLLNSLSPEQLVLTLLEAEPPNVLVSRP  240
SMPFTEASMMMSLTKLADKELVHMIGWAKKIPGFVELSLL  280
DQVRLLESCWMEVLMVGLMWRSIDHPGKLIFAPDLVLDRD  320
EGKCVEGILEIFDMLLATTARFRELKLQHKEYLCVKAMIL  360
LNSSMYHLATASQEAESSRKLTHLLNAVTDALVWVISKSR  400
ISSQQQSVRLANLLMLLSHVRHISNKGMEHLLSMKCKNVV  440
PVYDLLLEMLNAHTLRGYKSSISGSGCCSTEDSKSKEGSQ  480
NLQSQ.  486
```

FIG. 14A

```
   1  CTATGACATT CTACAGTCCT GCTGTGATGA ATTACAGCAT TCCCAGCAAT
  51  GTCACTAACT TGGAAGGTGG GCCTGGTCGG CAGACCACAA GCCCAAATGT
 101  GTTGTGGCCA ACACCTGGGC ACCTTTCTCC TTTAGTGGTC CATCGCCAGT
 151  TATCACATCT GTATGCGGAA CCTCAAAAGA GTCCCTGGTG TGAAGCAAGA
 201  TCGCTAGAAC ACACCTTACC TGTAAACAGA GAGACACTGA AAAGGAAGGT
 251  TAGTGGGAAC CGTTGCGCCA GCCCTGTTAC TGGTCCAGGT TCAAAGAGGG
 301  ATGCTCACTT CTGCGCTGTC TGCAGCGATT ACGCATCGGG ATATCACTAT
 351  GGAGTCTGGT CGTGTGAAGG ATGTAAGGCC TTTTTTAAAA GAAGCATTCA
 401  AGGACATAAT GATTATATTT GTCCAGCTAC AAATCAGTGT ACAATCGATA
 451  AAAACCGGCG CAAGAGCTGC CAGGCCTGCC GACTTCGGAA GTGTTACGAA
 501  GTGGGAATGG TGAAGTGTGG CTCCGGAGA GAGAGATGTG GGTACCGCCT
 551  TGTGCGGAGA CAGAGAAGTG CCGACGAGCA GCTGCACTGT GCCGGCAAGG
 601  CCAAGAGAAG TGGCGGCCAC GCGCCCGAG TGCGGGAGCT GCTGCTGGAC
 651  GCCCTGAGCC CCGAGCAGCT AGTGCTCACC CTCCTGGAGG CTGAGCCGCC
 701  CCATGTGCTG ATCAGCCGCC CCAGTGCGCC CTTCACGAG GCCTCCATGA
 751  TGATGTCCCT GACCAAGTTG GCCGACAAGG AGTTGGTACA CATGATCAGC
 801  TGGGCCAAGA AGATTCCCGG CTTTGTGGAG CTCAGCCTGT TCGACCAAGT
 851  GCGGCTCTTG GAGAGCTGTT GGATGGAGGT GTTAATGATG GGCTGATGT
 901  GGCGCTCAAT TGACCACCCC GGCAAGCTCA TCTTTGCTCC AGATCTTGTT
 951  CTGGACAGGG ATGAGGGGAA ATGCGTAGAA GGAATTCTGG AAATCTTTGA
1001  CATGCTCCTG GCAACTACTT CAAGGTTTCG AGAGTTAAAA CTCCAACACA
1051  AAGAATATCT CTGTGTCAAG GCCATGATCC TGCTCAATTC CAGTATGTAC
1101  CCTCTGGTCA CAGCGACCCA GGATGCTGAC AGCAGCCGGA AGCTGGCTCA
1151  CTTGCTGAAC GCCGTGACCG ATGCTTTGGT TTGGGTGATT GCCAAGAGCG
1201  GCATCTCCTC CCAGCAGCAA TCCATGCGCC TGGCTAACCT CCTGATGCTC
1251  CTGTCCCACG TCAGGCATGC GAGTAACAAG GCATGGAAC ATCTGCTCAA
1301  CATGAAGTGC AAAAATGTGG TCCAGTGTA TGACCTGCTG CTGGAGATGC
1351  TGAATGCCCA CGTGCTTCGC GGGTGCAAGT CCTCCATCAC GGGGTCCGAG
1401  TGCAGCCCGG CAGAGGACAG TAAAAGCAAA GAGGGCTCCC AGAACCTACA
1451  GTCTCAGTGA
```

FIG. 13B

```
ATGGCATTCTAC AGTCCTGCTGTG ATGAACTACAGT GTTCCCAGCAGC ACCGGTAACCTG GAAGGTGGGCCT    72
GTTCGCCAGACT GCAAGCCCAAAT GTGCTATGGCCA ACTTCTGaCACAC CTCTCTCCTTTA GCCACCACTGC   144
CAATCATCGCTT CTCTATGCAGAA CCTCAAAAGAGT CCTGGTGTGAA GCAAGATCACTA GAACACACCTTG   216
CCTGTAAACAGA GAGACCCTGAAG AGGAAGCTTGGC GCCAGCCCTGTT GCCAGCCCTGTT ACTAGTCCAAgC   288
ACCAAGAGGGAT GCTCACTTCTGT GCCGTCTGCAGT GATTATGCATCT GGTATCATTAC GGTGTCTGGTCc   360
TGTGAAGGATGT AAGGCCTTTTTT AAAAGAAGCATT GCCGTCTGCAGT GACTATATCTGT CCAGCCACGAAT   432
CAGTGTACGATA GACAAGAACCGg CGTAAAAACTGC CAGGCCTGCCGA CTTCGCAAgTGT TACGAAGTAGGA   504
ATGGTCAAGTGT GGATCCAGGAGA GAAAGGTGTGGG TACCGAATAGTA CGAAGACAGAGA AGTGCCAGCGAG   576
CAGGTGCATTGC CTGAACAAAGCC AAGAGAACCAGT GGGCACACACCC CGGGTGAAGGAG CTACTGCTGAAC   648
TCTCTGAGTCCC GAGCAGCTGGTG CTCACCCTGCTG GAAGCTGAGCGC CCCAATGTGCTA GTGAGTCGTCCC   720
AGCATGCCCTTC ACCGAGGCCTCC ATGATGATGTCC CTTACGAAGTCC GCTGACAAGAA CTGGTGCACATG   792
ATTGGCTGGGCC AAGAAAATCCCT GGCTTTGTGGAG CTCAGCCTGTTG GACCAAGTCCGC CTCTTGGAAAGC   864
TGCTGGATGGAG GTGCTGATGGTG GGGCTGATGTGG CGCTCCATCGAC CACCCCGGCAAG CTCATCTTTGCT   936
CCAGATCCTCGT CTGGACAGGGAT GAgGGAAGTGC GTgGAAATCTTT GaCATGCTCCTG CTGGAGCTCCTG  1008
GCgACGACGGCA CGGTTCCGTGAG TTAAAACTGCAG CACAAGAATAT CTGTGTGTGAAG GCCATGATTCTC  1080
CTCAACTCCAGT ATGTACCACTTG GCTACCGCAAGC CAGGAAGCAGAG AGTAGCCGGAAG CTGACACACCTA  1152
TTGAACGCAGTG ACAGATGCCCTG GTCGTGGGTGATT TCGAAGAGTAGA ATCTCTTCCAG CAGCAGTCAgTC  1224
CGTCTGGCCAAC CTCCTGATGCTt CTTtCTCATGTC AGGCACATCAGT AACaAgGGCATG GAACATCTGCTC  1296
AGCATGAAGTGC AAAAATGTGGTC CCGGTGTACGAC CTGCTGCTGGAG ATGCTGAATGCT CACACGCTTCGA  1368
GGGTACAAGTCC TCAATCTCGGGg TCTGgGTGCTGC TCGACAGAGGAC AGTAAGAGCAAA GAGGGCTCCCAG  1440
AACCTCCCAGTCT CAGTGA    1458
```

FIG. 14B

| CPD | logIC50 hERα | log IC50 rERβ | IC50 (nM) hERα | IC50(nM) rERβ | Ki (nM) hERα | Ki (nM) rERβ | RBA(%), Ki hERα | RBA(%), Ki rERβ | RBA(%), IC50 hERα | RBA(%), IC50 rERβ |
|---|---|---|---|---|---|---|---|---|---|---|
| DiHydroapoandrstenedione | -6.31 | -6.73 | 485.29 | 187.11 | 245.31 | 163.33 | 0.027 | 0.115 | 0.027 | 0.115 |
| Testosterone | -5.00 | -5.66 | 10000.00 | 2187.76 | 5750.97 | 1937.70 | 0.001 | 0.010 | 0.001 | 0.010 |
| DiHydrotestosterone | -6.36 | -7.08 | 436.52 | 83.95 | 220.66 | 73.28 | 0.030 | 0.256 | 0.030 | 0.256 |
| 4-OH-Estradiol | -8.78 | -8.67 | 1.66 | 2.14 | 0.95 | 1.89 | 6.934 | 9.892 | 7.889 | 10.037 |
| 19-Nor testosterone | -5.82 | -7.22 | 1513.56 | 60.12 | 765.10 | 52.48 | 0.009 | 0.357 | 0.009 | 0.357 |
| 5β-Androstanedione | >-4 | >-4 | >100000 | >100000 | >100000 | >100000 | <0.0002% | <0.0002% | <0.0002% | <0.0002% |
| Cyproteroneacetate | >-4 | >-4 | >100000 | >100000 | >100000 | >100000 | <0.0002% | <0.0002% | <0.0002% | <0.0002% |
| δ-4 androstene 3,17, dione | >-4 | >-4 | >100000 | >100000 | >100000 | >100000 | <0.0002% | <0.0002% | <0.0002% | <0.0002% |
| Progesterone | >-4 | >-4 | >100000 | >100000 | >100000 | >100000 | <0.0002% | <0.0002% | <0.0002% | <0.0002% |
| Corticosterone | >-4 | >-4 | >100000 | >100000 | >100000 | >100000 | <0.0002% | <0.0002% | <0.0002% | <0.0002% |
| Genistein | -8.35 | -9.41 | 4.47 | 0.39 | 2.57 | 0.34 | 2.576 | 54.361 | 2.931 | 55.157 |
| β-sitosterol | >-4 | >-4 | >100000 | >100000 | <0.0002% | <0.0002% | <0.0002% | <0.0002% | <0.0002% | <0.0002% |
| norethynodrel | -7.53 | -7.20 | 29.51 | 63.10 | 14.22 | 53.09 | 0.466 | 0.353 | 0.444 | 0.340 |
| norethindrone | -6.50 | -5.89 | 316.23 | 1288.25 | 152.32 | 1083.89 | 0.043 | 0.017 | 0.041 | 0.017 |
| β-zearalanol | -8.89 | -9.00 | 1.29 | 0.99 | 0.78 | 0.87 | 8.457 | 21.465 | 10.162 | 21.657 |
| D-4 androsten 3β,17β-diol | -7.33 | -7.64 | 46.77 | 22.91 | 23.39 | 18.71 | 0.283 | 1.001 | 0.280 | 0.937 |
| dienestrol | -10.03 | -10.46 | 0.09 | 0.03 | 0.05 | 0.03 | 140.523 | 661.418 | 138.995 | 618.871 |
| Methoxychlor | -5.45 | -6.96 | 3548.13 | 109.65 | 1774.07 | 89.56 | 0.004 | 0.209 | 0.004 | 0.196 |
| Bisphenol A | -6.41 | -7.37 | 389.05 | 42.66 | 194.52 | 34.84 | 0.034 | 0.538 | 0.034 | 0.503 |
| Ecdysterone* | >-4 | >-4 | >100000 | >100000 | >100000 | >100000 | <0.0002% | <0.0002% | <0.0002% | <0.0002% |
| Eudesmine | >-4 | >-4 | >100000 | >100000 | >100000 | >100000 | <0.0002% | <0.0002% | <0.0002% | <0.0002% |
| Lapidine | >-4 | >-4 | >100000 | >100000 | >100000 | >100000 | <0.0002% | <0.0002% | <0.0002% | <0.0002% |
| Tschimgine | -7.18 | -6.63 | 66.07 | 234.42 | 40.13 | 206.47 | 0.165 | 0.091 | 0.198 | 0.092 |
| Tschimganidine | -7.87 | -6.45 | 13.49 | 354.81 | 8.19 | 312.50 | 0.808 | 0.060 | 0.971 | 0.060 |
| Ferutinine | -9.10 | -9.56 | 0.79 | 0.27 | 0.40 | 0.24 | 16.623 | 78.091 | 16.623 | 78.091 |
| Coumestrol | -9.65 | -10.12 | 0.22 | 0.08 | 0.14 | 0.07 | 48.665 | 282.307 | 58.479 | 284.839 |
| Nafoxidine | -9.32 | -9.05 | 0.48 | 0.90 | 0.24 | 0.78 | 27.530 | 23.966 | 27.530 | 23.966 |
| 16a-Br-E2 | -9.88 | -9.67 | 0.13 | 0.21 | 0.07 | 0.19 | 100.000 | 100.000 | 100.000 | 100.000 |
| 17a-E2 | -9.44 | -8.88 | 0.36 | 1.32 | 0.22 | 1.16 | 30.006 | 16.133 | 36.058 | 16.278 |
| 17β-E2 | -9.68 | -9.87 | 0.21 | 0.13 | 0.13 | 0.12 | 52.145 | 157.660 | 62.661 | 159.074 |

*)β-Ecdysone, 20_Hydroxyecdysone
RBA-values derived from 16a-Br-E2 (100%)

FIG. 15

ORPHAN RECEPTOR

CROSS-REFERENCE TO RELATED APPLICATIONS

This application is a Continuation of U.S. Ser. No. 10/083,807 filed Feb. 27, 2002, now abandoned, which is a Continuation of U.S. Ser. No. 09/333,057 filed Jun. 14, 1999, now abandoned, which is a Continuation of U.S. Ser. No. 08/836,620, filed May 8, 1997, now U.S. Pat. No. 5,958,710, which is a 371 and claims the benefit of International Application Serial No. PCT/EP96/03933 filed Sep. 9, 1996. All the above applications are incorporated by reference in their entireties.

This invention relates to cellular nuclear receptors and their uses.

A large family of nuclear receptors which confer cells with responsiveness to molecules such as retinoid acid, vitamin D, steroid hormones and thyroid hormones has been identified. Extensive studies have shown that the members of this superfamily of nuclear receptors activate and/or repress gene transcription through direct binding to discrete cis-acting elements termed "hormone response elements" (HRE). It has been shown that these HRE's comprise repeats of consensus palindromic hexanucleotide DNA motifs. The specificity of the HRE's is determined by the orientation of, and spacing between, halfsites (i.e. half a palindromic sequence)(Umenesono K., et al, 1991 Cell 65, 1255–1266).

Specific DNA binding is mediated by a strongly-conserved DNA binding domain, containing two zinc fingers, which is conserved among all thus discovered nuclear receptors. Three amino acids at the C-terminal base of the first zinc finger (known as the "P-box") are important for the recognition of the half site nucleotide sequence. Members of the nuclear receptor superfamily have been classified into different groups on the basis of the amino acid sequence within the P box.

All members of the nuclear receptor superfamily also contain a hypervariable N-terminal domain and a ligand-binding domain containing some "patches" of conserved sequence. One of these is called the "Ti-domain".

Molecules which are thought to be nuclear receptors, as they are structurally related to characterised receptors, but for which no ligand has been found, are termed "orphan receptors". Many such orphan receptors have been identified (see for example Evans R. M. (1988) Science 240, 889–895 and O'Malley, B. (1990) Mol. Endocrinol. 4 363–369)

We have now unexpectedly identified, initially in rat a new orphan receptor, which is related to the known estrogen receptor ERα, and which we have designated "ERβ" (specifically "rERβ" in rat). In this specification "Erβ" will be used to refer to the receptors hERβ or rERβ or related receptors. The nucleotide and amino acid sequences of rERβ have now been determined and are shown in FIG. 1. We have also identified a human Erβ—"hERβ", the amino acid DNA and sequences of which are shown in FIGS. 13A and 13B respectively.

According to one aspect of the invention there is provided a novel estrogen receptor-related nuclear receptor, hereinafter termed "ERβ" having the amino acid sequence of FIG. 1, FIG. 13A or 16A or substantially the same amino acid sequence as the amino acid sequence shown in FIG. 1, 13A or 16A or an amino acid sequence functionally similar to those sequence. The isolated receptor may be particularly useful in the search for molecules for use in treatment of diseases or conditions such as cardiovascular diseases, central nervous system diseases or conditions or osteoporosis, prostate cancer or benign prostatic hyperplasia.

The receptor of the invention may also be used in the testing of environmental chemicals for estrogenic activity. There has been increasing concern over the effect of various chemicals released into the environment on the reproduction of humans and animals. Threats to the reproductive capabilities of birds, fish, reptiles, and some mammals have become evident and similar effects in humans have been proposed. Substantial evidence is now emerging which shows that exposure to certain chemicals during critical periods of foetal life may distort the development of the reproductive organs and the immune and nervous systems. On the basis of possible parallels between actual wildlife effects, seen for example in birds and seals living in highly polluted areas, and proposed effects in humans, in combination with documented human reproductive effects caused by prenatal exposure to the pharmaceutical estrogen, diethyl stilbestrol (DES), "estrogenic" chemicals have been proposed to threaten the reproductive capability of both animals and humans. Among the chemicals known or suspected to act as estrogen mimics on the human body, or in other ways disturb the human endocrine system, there are several which have already been identified as environmental hazards. Among the chemicals that have been mentioned as potential causes of disruption of reproductive function in animals and humans are chlorinated organic compounds such dieldrin, endosulfans, chlordanes, endrins, aldrin, DDT and some PCBs, plastics such as Bisphenol A, phthalates and non-ylphenol, and aromatic hydrocarbons. Some of the proposed effects on humans have been suggested to be due to an increasing exposure to environmental estrogens—in fact, exposure to chemical compounds to which higher organisms during the foetal period react in a way that is similar to when they are exposed to high dosages of estrogens. The effects are manifested by for example perturbations of the sex characteristics and impaired reproductive potential. In humans, elevated risks of breast cancer and other hormone-related disease has also been discussed as possible effects. In addition, to the documented "estrogenic" effects, it has recently been demonstrated that environmental pollutants may also act on hormonal pathways other than the estrogenic pathway—it has been shown that p,p'—DDE the main metabolite of DDT (also in humans) is a fairly anti-androgenic agent (Kelce W. R. et al Nature 1995 375:581–585). Epidemiological studies on these issues are, however, presently difficult to interpret. Nevertheless, there is a growing opinion against these potentially hormone disrupting chemicals, and very palpable public and environmental demand for the governmental agencies and industry to act. In view of the similarities between the receptor of the present invention, Erβ and the classical estrogen receptor, Erβ may be used in the testing of chemicals for estrogenic effect.

An amino acid sequence functionally-similar to the sequence shown in FIG. 1, 13A or 14A may be from a different mammalian species.

An amino acid sequence which is more than about 89%, identical with the sequence shown in FIG. 1, 13A or 14A is substantially the same amino acid sequence for the purposes of the present application. Preferably, the amino acid sequences is more than about 95% identical with the sequence shown in FIG. 1, 13A or 14A.

According to another aspect of the invention there is provided a DNA sequence encoding a nuclear receptor according to the first aspect of the invention. Preferably, the DNA sequence is that given in FIG. 1, 13A or 14A or is a DNA sequence encoding a protein or polypeptide having the functionality of ERβ.

ERβ is unique in that it is extremely homologous to the rat estrogen receptor, in particular in its DNA binding domain. It appears that ERβ has a very limited tissue distribution. In female rats, it appears to be present only in the ovaries, and in male rats in the prostate and testes. As these tissues are classic targets for estrogen action, it can be deduced that ERβ may mediate some of the effects of estrogen.

The different ligand specificity of ERα and ERβ may be exploited to design pharmaceutical agents which are selective for either receptor. In particular, the differences in ligand specificity may be used to develop drugs that specifically target cardiovascular disease in postmenopausal women or osteoporosis.

The nuclear receptor of the invention, ERβ, a method of producing it, and tests on its functionality will now be described, by way of example only, with reference to the accompanying drawings, FIGS. 1 to 15 in which:

FIG. 1 shows the amino acid sequence of ERβ and the nucleotide sequence of the gene encoding it;

FIG. 2A is a phylogenetic tree showing the evolution of ERβ and other receptors;

FIG. 2B shows the homology between the different domains in ERβ and certain other receptors;

FIG. 2C is an alignment of the amino acid sequence in the ligand binding domains of rERβ, rERα, mERα and hERα;

FIG. 2D is an alignment of the amino acid sequence in the DNA binding domains of rERβ, rERα, mERα and hERα;

Figure 3A:
FIG. 3A is a film autoradiograph of prostate gland showing strong expression of a clone of the receptor of the invention, clone 29.
Figure 3B:
FIG. 3B is a darkfield image showing prominent signal for clone 29 in epithelium (e) of prostatic alveoli. The stroma(s) exhibit(s) weaker signal.
Figure 3C:
FIG. 3C is a bipolarization image of cresyl violet counterstained section showing silver grains over epithelium (e), whereas the stroma(s) contain(s) less grains.
Figure 4A:
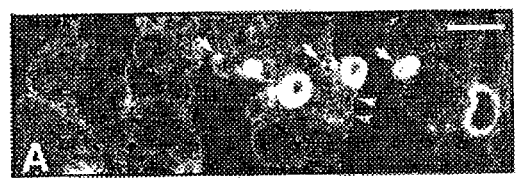
Figure 4B:
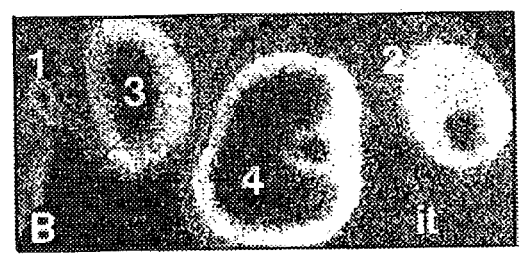
Figure 4C:
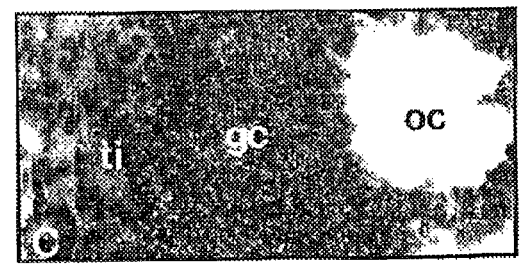
Figure 5A:
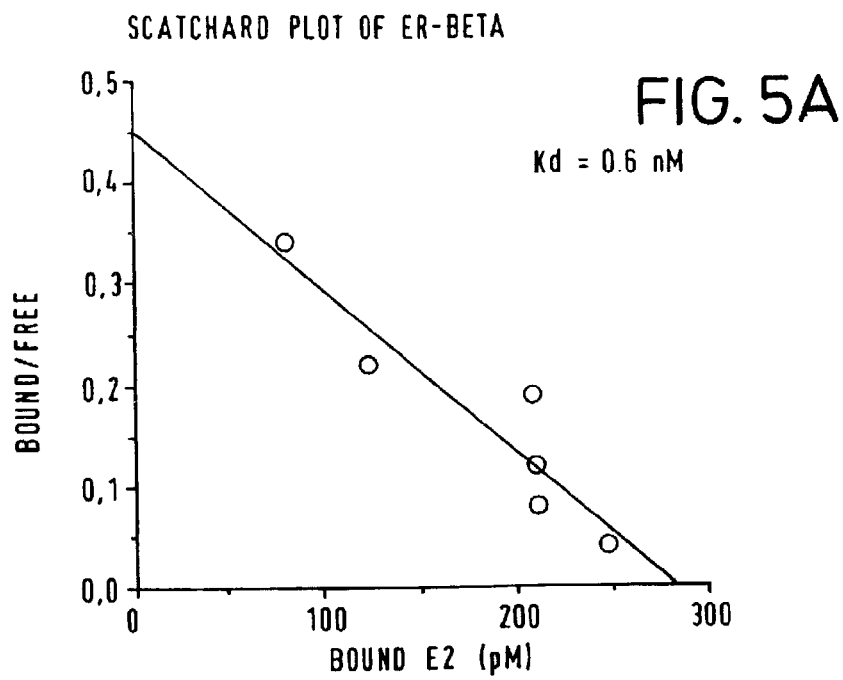
Figure 5B:
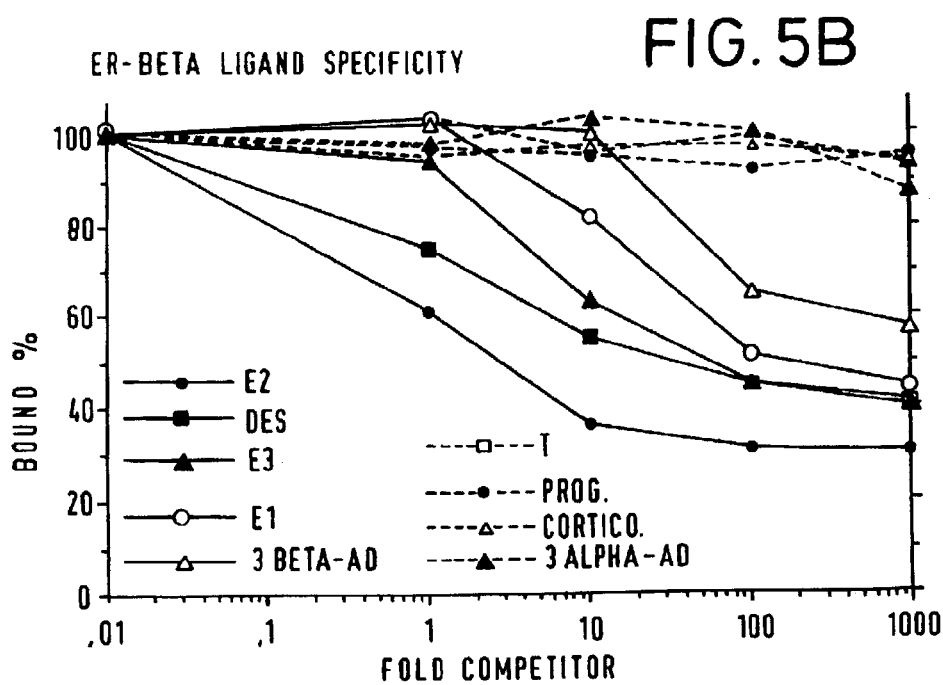
Figure 5C:
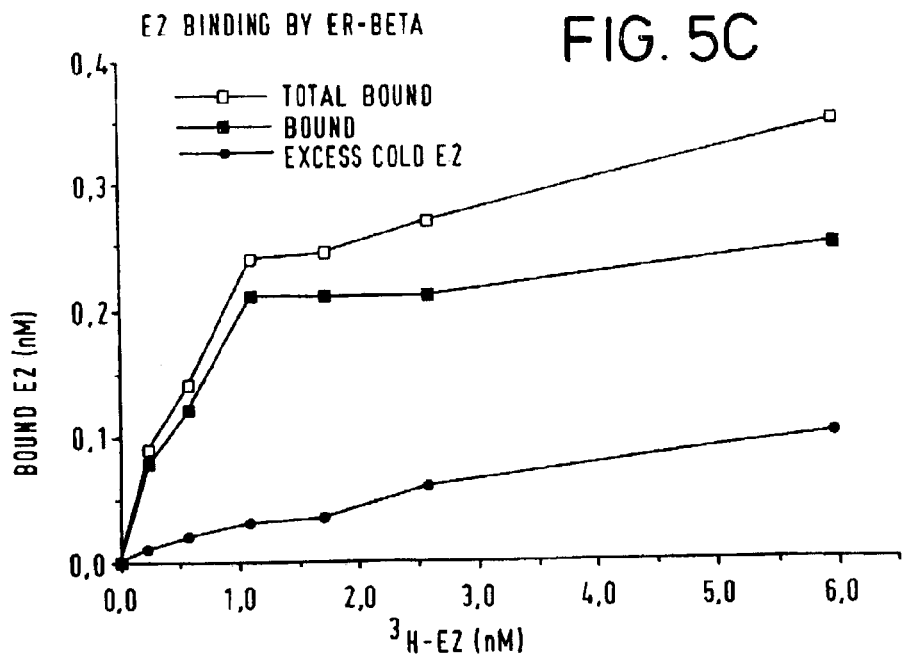
Figure 6:
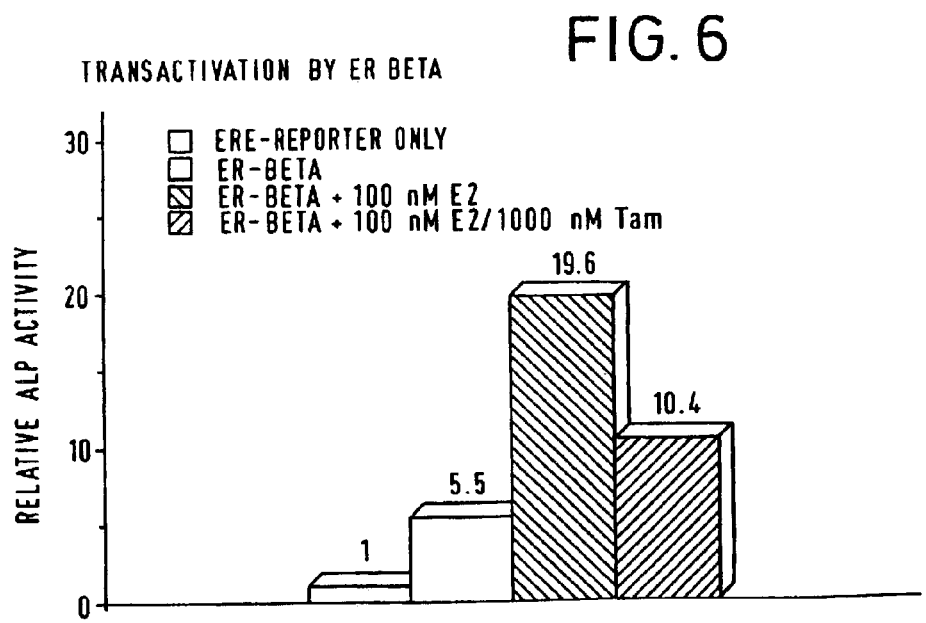
Figure 7:
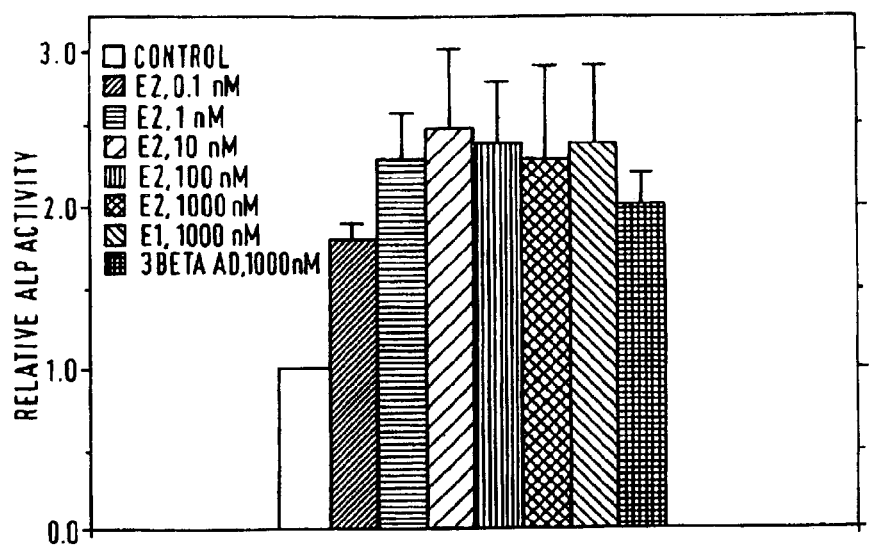
Figure 7A:
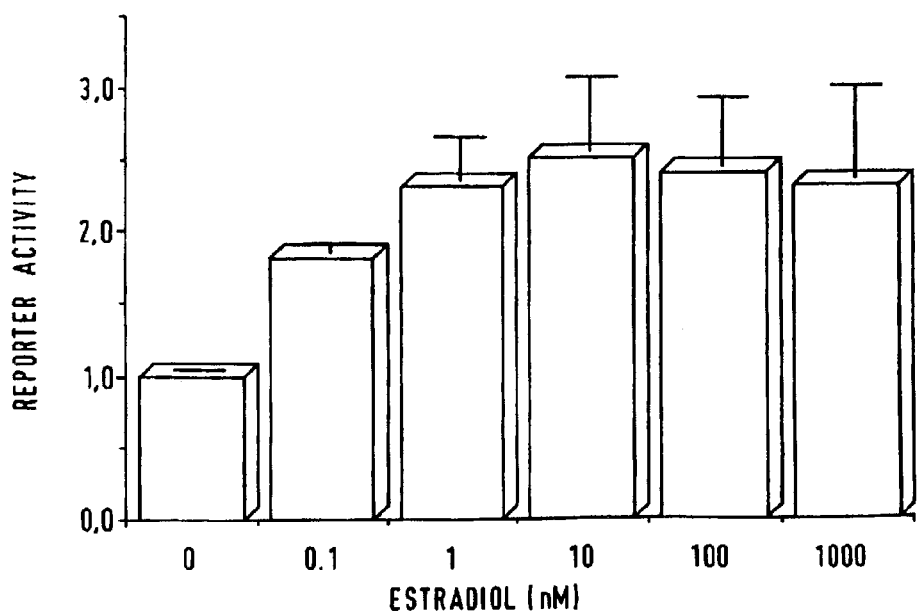
Figure 8:
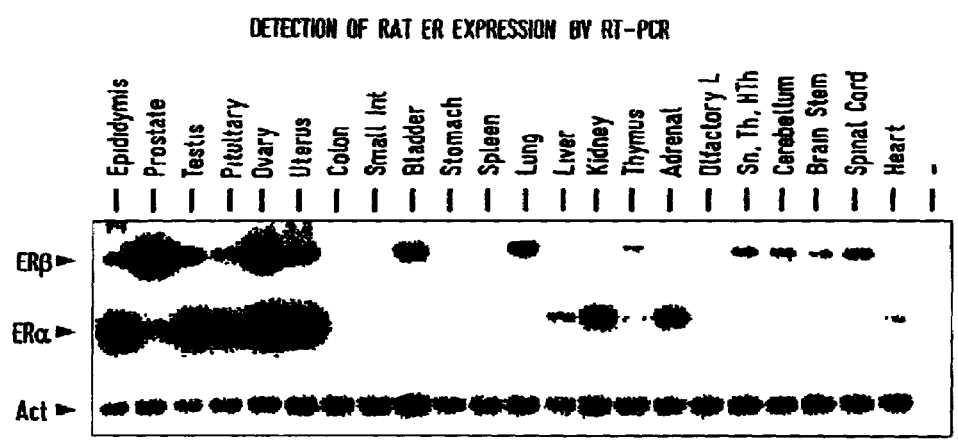
Figure 9:
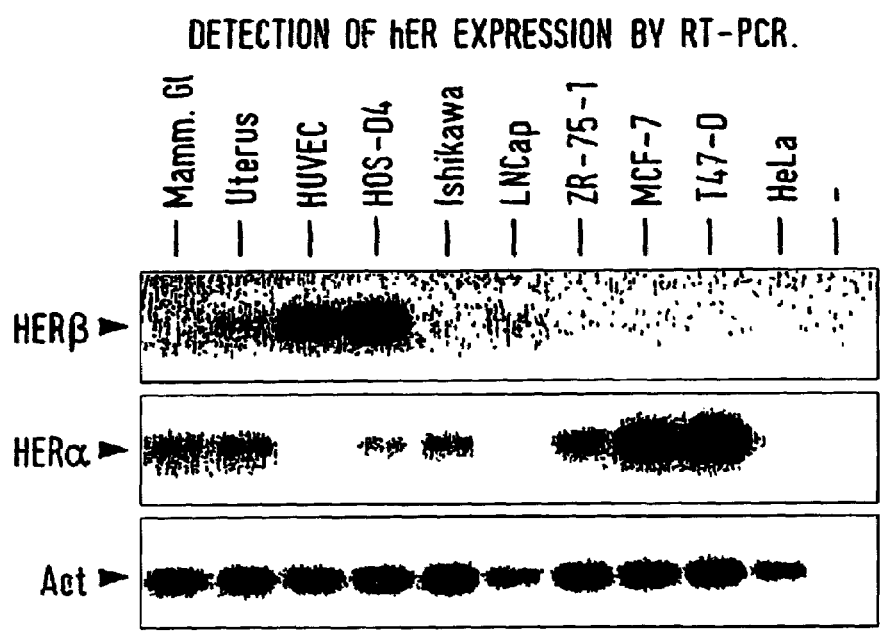

The bar represents 0.7 mm for FIG. 3A, 200 μm for FIG. 3B and 30 μm for FIG. 3C;

FIG. 4A shows a film autoradiograph of ovary showing strong expression of clone 29 in follicles at different developmental stages (some are indicated by arrows). The interstitial tissue (arrowheads) shows low signal;

FIG. 4B shows a darkfield image showing high expression of clone 29 in granular cells of primary (1), secondary (2), tertiary (3) and mature (4) follicles. Low signal is present in interstitial tissue (it);

FIG. 4C is a bipolarization image of ovary a showing strong signal in granular cells (gc), whereas the oocyte (oc) and the cainterna (ti) are devoid of clear signal;

The bar represents 0.9 mm for FIG. 4A, 140 μm for FIG. 4B and 50 μm for FIG. 4C;

FIG. 5A illustrates the results of saturation ligand binding analysis of cloned ERβ;

FIG. 5B illustrates the specificity of ligand binding by cloned ERβ;

FIG. 5C illustrates E2 binding by ERβ;

FIG. 6 illustrates the activation of transcription by cloned ERβ;

FIGS. 7 and 7A illustrates stimulation by various ligands by cloned ERβ;

FIG. 8 illustrates the results of RT-PCR experiments on the expression of rat estrogen receptors;

FIG. 9 illustrates the results of RT-PCR experiments on the expression of human Erβ (hERβ);

FIG. 10A is a Hill plot comparing binding of $^{125}$I-E2 by hERα and rERβ;

FIG. 10B is a Scatchard plot comparing binding of $^{125}$I-E2 by hERα and rERβ;

FIG. 11A illustrates the relative binding affinity of hERα and rERβ for various ligands;

FIG. 11B is a detail of FIG. 12A;

Figure 12:
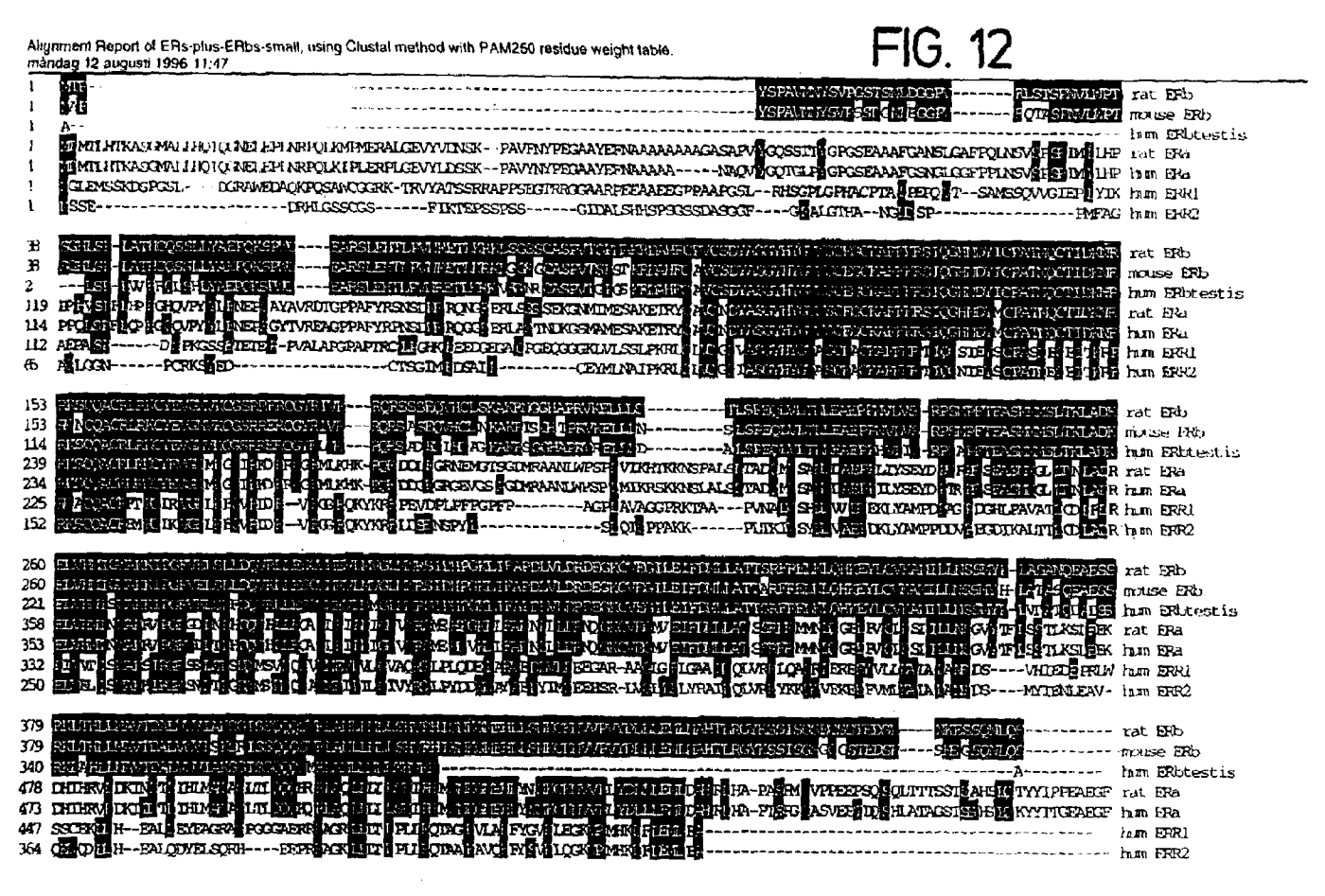

FIG. 12 is an alignment of various estrogen receptors;

FIG. 13A shows the amino acid sequence of human ERβ;

FIG. 13B shows the DNA sequence of human Erβ;

FIG. 14A shows the amino acid sequence of mERβ;

FIG. 14B shows the DNA sequence of mouse Erβ; and

FIG. 15 illustrates ligand binding affinities for various phytoestrogens by ER's of the invention.

A. CLONING OF RAT ERβ

1. PCR-Amplification and Complementary DNA Cloning.

A set of degenerate primers (DBD 1, 2, 3 and WAK/FAK) were designed previously according to the most highly conserved sequences of the DNA-binding domain (P-box) and ligand binding domain (Ti-stretch) of members of the nuclear receptor family (Enmark, E., Kainu, T., Pelto-Huikko, M., & Gustafsson, J-Å (1994) *Biochem. Biophys. Res. Commun.* 204, 49–56). Single strand complementary DNA reverse transcribed from rat prostate total RNA was employed with the primers in PCR reactions as described in Enmark, E., Kainu, T., Pelto-Huikko, M., & Gustafsson, J-Å (1994) *Biochem. Biophys. Res. Commun.* 204, 49–56. The amplification products were separated on a 2% low melting agarose gel and DNA products between 400 and 700 bp were isolated from the gel and ligated to TA cloning vector (Invitrogen). As alternatives, we also used the RP-I/IRP-2 and DBD66–100/DBD210–238 primer sets in the DNA-binding domain of nuclear receptors exactly as described by Hirose T., Fijimoto, W., Yamaai, T., Kim, K. H., Matsuura, H., & Jetten, A. M. (1994) *Mol. Endocrinol.* 8, 1667–1677 and Chang, C., Lopes Da Silva, S., Ideta, R., Lee, Y., Yeh, S., & Burbach, J. P. H. (1994) *Proc. Natl. Acad. Sci.* 91, 6040–6044 respectively. Clone number 29 (obtained with the DBD-WAK/FAK set) with a length of 462 bp showed high homology (65%) with the rat estrogen receptor cDNA (65%), which was previously cloned from rat uterus (Koike, S., Sakai, M., & Muramatsu, M. (1987) *Nucleic Acids Res* 15, 2499–2513). The amino acid residues predicted by clone 29 DNA sequences suggested that this DNA fragment encoded part of the DNA-binding domain, hinge region and the beginning of the ligand binding domain of a novel member of the nuclear receptor family. Two PCR primers (FIG. 1) were used to generate a probe of 204 bp consisting of the hinge region of the novel receptor, which was used to screen a rat prostate cDNA library (Clontech gt10) under stringent conditions resulting in four strongly positive clones with a size of 0.9 kb, 1.8 kb, 2.5 kb and 5–6 kb respectively. The clone of 2.5 kb was sequenced and FIG. 1 shows the nucleotide sequence determined in the core facility (CyberGene AB) by cycle sequencing using fluorescent terminators (Applied Biosystems) on both strands, with a series of internal primers and deduced amino acid sequence of clone 29. Two in frame ATG codons are located at nucleotide 424 and nucleotide 448, preceding by an in-frame stop codon at nucleotide 319, which suggests that they are possible start codons. The open reading frame encodes a protein of 485 amino acid residues (counted from the first methionine) with a calculated molecular weight of 54.2 kDa. Analysis of the proteins by synthesized by in-vitro translation from the clone 29 cRNA in rabbit reticulocyte lysate revealed a doublet protein band migrating at approximately 57 kDa on SDS-PAGE gels (data not shown), confirming the open reading frame. The doublet protein band is probably caused by the use of both ATG codons for initiation of protein synthesis. The amino acid sequence of clone 29 protein shows the characteristic zinc module DNA-binding domain, hinge region and a putative ligand binding domain, which are the characteristic features of members of the nuclear receptor family (Tsai, M-J., & O'Malley, B. W. (1994) *Ann. Rev. Biochem.* 63, 451–486; Härd, T., & Gustafsson, J-Å (1993) *Acc. Chem. Res.* 26, 644–650; Laudet, V., Hänni, C., Coli, J., Catzeflis, F., & Stehelin, D (1992) *EMBL J* 11, 1003–1012).

Protein sequence comparison with several representative members of the nuclear receptor family (FIG. 2) showed the clone 29 protein is most related to the rat estrogen receptor (ERα), cloned from uterus (Koike, S., Sakai, M., & Muramatsu, M. (1987) *Nucleic. Acids Res.* 15, 2499–2513), with 95% identity in the DNA-binding domain (amino acid residues 103–167) (Griffiths, K., Davies, P., Eaton, C. I., Harper, M. E., Turkes, A., & Peeling, W. B. (1991) in *Endocrine Dependent Tumours*, eds. Voigt, K-D. & Knabbe, C. (Raven Press), pp. 83–125). A number of functional characteristics have been identified within the DNA-binding domain of nuclear receptors (Härd, T., & Gustafsson, J-Å. (1993) *Acc. Chem. Res* 26, 644–650 and Zilliacus, J., Carlstedt-Duke, J., Gustafsson, J-Å., & Wright, A. P. H. (1994) *Proc. Natl. Acad. Sci. USA* 91, 4175–4179). The so-called P-box specifies nucleotide sequence recognition of the core half-site within the response element, while the D-box mediates dimerization between receptor monomers. The clone 29 protein P-box and D-box sequences of EGCKA and PATNQ, respectively, are identical to the corresponding boxes in ERα (Härd, T., & Gustafsson, J-Å. (1993) *Acc. Chem. Res* 26, 644–650 and Koike, S., Sakai, M., & Muramatsu, M. (1987) *Nucleic Acids Res.* 15, 2499–2513), thus predicting that clone 29 protein binds to ERE sequences.

The putative ligand binding domain (LBD) of clone 29 protein (amino acid residues 259–457) shows closest homology to the LBD of the rat ERα (FIG. 2), while the homology with the human ERR1 and ERR2 proteins (Giguere, V., Yang, N., Segui, P., & Evans R. M. (1988) *Nature* 331, 91–94) is considerably less. With the human, mouse and xenopus estrogen receptors the homology in the LBD is also around 55%, while the homology with the LBD of other steroid receptors is not significant (FIG. 2). Cysteine residue 530 in human ERα has been identified as the covalent attachment site of an estrogenic affinity label (Harlow, K. W., Smith D. N., Katzenellenbogen, J. A., Greene, G. L., & Katzenellenbogen, B. S. (1989) *J. Biol. Chem.* 264, 17476–17485). Interestingly, clone 29 protein (Cys-436) as well as the mouse, rat and xenopus ERαs have a cysteine residue at the corresponding position. Also, two other amino acid residues described to be close to or part of the ligand-binding pocket of the human ERα-LBD (Asp 426 and Gly 521) are conserved in the LBD of clone 29 protein, (Asp 333 and Gly 427) and in the LBD of ERαs from various species (20,21). The ligand-dependent transactivation function TAF-2 identified in ERα (Danielian, P. S., White, R., Lees, J. A., & Parker, M. G. (1992) *EMBO J.* 11, 1025–1033), which is believed to be involved in contacting other transcription factors and thereby influencing activation of transcription of tarteg genes, is almost completely conserved in clone 29 protein (amino acid residues 441–457). Steroid hormone receptors are phosphoproteins (Kuiper, G., & Brinkmann, A. O. (1994) *Mol. Cell. Endocrinol.* 100, 103–107), and several phosphorylation sites identified in the N-terminal domain and LBD of ERα (Arnold, S. F., Oboum, J. D., Jaffe, H., & Notides. A. C. (1995) *Mol. Endocrinol.* 9, 24–33 and Le Goff, P., Montano, M. M., Schodin, D. J., & Katzenellenbogen, B. S. (1994) *J. Biol. Chem.* 269, 4458–4466) are conserved in clone 29 protein (Ser 30 and 42, Tyr 443). Clone 29 protein consists of 485 amino acid residues while ERαs from human, mouse and rat consist of 590–600 amino acid residues. The main difference is a much shorter N-terminal domain in clone 29 protein i.e 103 amino acid residues as compared to 185–190 amino acid residues in the other receptor proteins. Also the non-conserved so-called F-domain at the C-terminal end of ERαs is 15 amino acid residues shorter in clone 29 protein. The cDNA insert of a positive clone of 2.6 kb was subcloned into the EcoR1 site of pBluescript (trademark) (Stratagene). The complete DNA sequence of clone 29 was determined (CyberGene AB) by cycle sequencing using fluorescent terminators (Applied Biosystems) on both strands, with a series of internal primers.

Figure 2C:
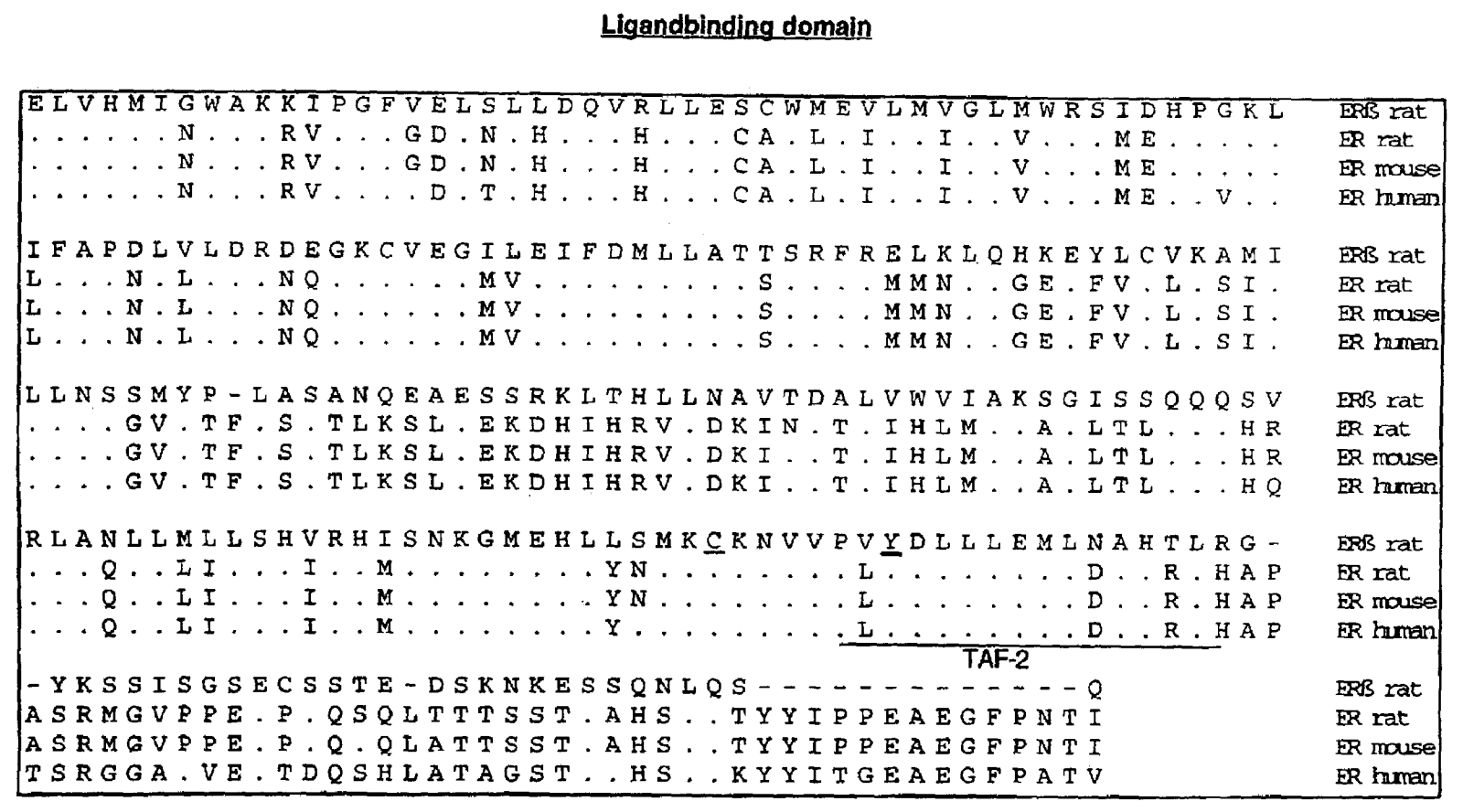

FIGS. 2C and 2D respectively compare the ligand and DNA binding domain of Erβ compared to rat, mouse and human Erα's.

2. Saturation Ligand Binding Analysis and Ligand Competition Studies:

Clone 29 cDNA was subcloned in pBluescript downstream of the T7 promoter to give p29-T7. Clone 29 protein was synthesized in vitro using the TnT-coupled reticulocyte lysate system (Promega). Translation reaction mixtures were diluted five times with TEDGMo buffer (40 mm Tris/HCl, pH 7.4, 1mM EDTA, 10% (v/v) glycerol, 10 mM Na$_2$MoO$_4$, 10 mM DTT) and 0.1 ml aliquots were incubated for 16 h at 8° C. with 0.3–6.2 nM [2,4,6,7-$^3$H]-17β-estradiol (NEN-Dupont; specific radioactivity 85 Ci/mmol) in the presence or absence of a 200-fold excess of unlabelled E2.

FIG. 5A illustrates the results of a saturation ligand analysis of clone 29 protein. Reticulocyte lysate containing clone 29 protein was incubated with 6 concentrations of [$^3$H]E2 between 0.3 and 6.0 nM. Parallel tubes contained an additional 200 fold of non-radioactive E2. Bound and free ligand were separated with a dextran-coated charcoal assay. The Kd (0.6 nM) was calculated from the slope of the line in the Scatchard plot shown (r=0.93), and the number of binding sites was extrapolated from the intercept on the abscissa (Bmax=1400 fmol/ml undiluted translation mixture).

For ligand competition studies diluted reticulocyte lysate was incubated with 5 nM [2,4,6,7-$^3$H]-17β-estradiol in the presence of either 0, 5, 50, 500 or 5,000 nM of non-radioactive E2, estrone, estriol, testosterone, progesterone, corticosterone, 5α-androstane-3β,17β-diol, 5α-androstane-3α,17β,-diol and diethylstilbestrol (DCES) for 16 h at 8° C. Bound and unbound steroids were separated with a dextran-coated charcoal assay (Ekman, P., Barrack, E. R., Greene, G. L., Jensen, E. V., & Walsh, P. C. (1983) *J. Clin. Endocrinol Metab.* 57, 166–176).

FIG. 5B illustrates the specificity of ligand binding by clone 29 protein. Reticulocyte lysate containing clone 29 protein was equilibrated for 16 h with 5 nM [$^3$H]E2 and the indicated fold excess of competitors. Data represent [$^3$H]E2 bound in the presence of unlabelled E2, testosterone (T), progesterone (prog), corticosterone (cortico), estrone (E1), diethylstilbestrol (DES), 5α-androstane-3α, 17β-diol (3α-AD), 5α-androstane-3β, 17β-diol (3β-AD) and estriol (E3). [$^3$H]E2 binding in the absence of competitor was set at 100%.

3. In-Situ Hybridisation:

In-situ hybridisation was carried out as previously described (Dagerlind Å., Friberg, K., Bean, A. J., & Hökfelt, T (1992) *Histochemistry* 98, 39–49). Briefly, two oligonucleotide probes directed against nucleotides 994–1041 and 1981–2031 were each labelled at the 3'-end with $^{33}$P-dATP using terminal deoxynucleotidyltransferase (Amersham, UK). Adult male and female Sprague-Dawley rats (age 2 to 3 months n=10) were used for this study. The rats were decapitated and the tissues were rapidly excised and frozen on dry ice. The tissues were sectioned in a Microm HM500 cryostat at 14 μm and thawed onto Probe-On glass slides (Fisher Scientific, PA, USA). The slides were stored at −20° C. until used. The slides were incubated in humidified boxes at 42° C. for 18 h with 1×10$^6$ cpm of the probe in a hybridization solution containing 50% formamide, 4×SSC (1×SSC=0.15 M NaCl, 0.015 M sodium citrate), 1× Denhardt (0.02% BSA, 0.02% Ficoll, 0.02% PVP), 1% sarkosyl, 0.02 M sodium phosphate (pH 7.), 10% dextran-sulphate, 500 μg/ml salmon sperm DNA and 200 mM DTT. Slides were subsequently rinsed in 1×SSC at 55° C. for 60 min with four changes of SSC and finally in 1×SSC starting at 55° C. and slowly cooled to room temperature, transferred through distilled water and briefly dehydrated in 50% and 95% ethanol for 30 sec each, air-dried, and covered with Amersham β-man autoradiography film for 15 to 30 days. Alternatively the slides were dipped in Kodak NTB2 nuclear track emulsion (diluted 1:1 with distilled water) and exposed for 30 to 60 days at 4° C. Finally, the sections were stained with cresyl violet.

Clear expression of clone 29 was observed in the reproductive tract of both male and female rats, while in all other rat tissues the expression was very low or below the level of detection with in-situ hybridisation (not shown). In male reproductive organs high expression was seen in the prostate gland (FIG. 3), while very low expression was observed in testis, epididymis and vesicula seminalis (not shown). In dipped sections, expression was clearly visible in prostate epithelial cells (secreting alveoli) while the expression in smooth muscle cells and fibroblasts in the stroma was low (FIG. 3). In female reproductive organs expression was seen in the ovary (FIG. 4), while uterus and vagina were negative (not shown). In dipped sections high expression was seen in the granulosa cell layer of primary, secondary and mature follicles (FIG. 4), whereas primordial follicles, oocytes and corpora lutea appeared completely negative. Low expression was seen in the interstitial cells of the ovary. Both anti-sense oligonucleotide probes used produced similar results. Addition of a 100 fold excess of the respective unlabelled oligonucleotide probes during the hybridisation reactions abolished all signals.

4. Transactivation Analysis in CHO-Cells:

The expression vector pCMV29 was constructed by inserting the 2.6 kb clone 29 fragment in the EcoRI site of the expression vector pCMV5 (Andersson, S., Davis, D.L., Dahlbäck, H., Jörnvall, H., & Russell, D.W. (1989) *J. Biol. Chem.* 264, 8222–8229). The pERE-ALP reporter construct contains a secreted form of the plancental alkaline phosphatase gene (Berger, J., Hauber, J., Hauber, R., Geiger, R., & Cullen, B.R. (1988) *Gene* 66 1–10) and the MMTV-LTR in which the glucocorticoid response elements were replaced by the vitellogenin promoter estrogen response element (ERE). The vector pCMV29 containing the clone 29 fragment was deposited with NCIMB, Ferguson Building, Craibstone Estate, Bucksburn, Aberdeen, Scotland, UK AB21 9YA in accordance with the Budapest Treaty on the International Recognition of the Deposit of Microorganisms for the Purposes of Patent Procedure on 26 May 2006, under accession No. NCIMB 41404. The deposit was named "*Escherichia coli* DH5 prat ER (CmV29)". All restrictions on the availability to the public of the material deposited will be irrevocably removed upon the granting of a patent.

CHO-K1 cells were seeded in 12-well plates at approximately 1.7×10$^5$ cells per well in phenol-red free Ham F12 medium with 5% FCS (dextran-coated charcoal treated) and 2 mM Lglutamine. After 24 h the cells were transfected with 250 ng pERE-ALP vector and 50 ng pCMV29 using lipofectamine (Gibco) according to the manufacturer's instructions. After five hours of incubation the cells were washed and refed with 0.5 ml phenol-red free Coon's F-12 medium containing 5% serum substitute (SRC 3000, Tissue Culture Services Ltd., Botolph Claydon, Buckingham, UK) 2 mM Lglutamine and 50 μg/ml gentamicin plus hormones as indicated. After 48 h the medium was assayed for alkaline phosphatase (ALP) activity by a chemiluminescence assay. A 10 μl aliquot of the cell culture medium was mixed with 200 μl assay buffer (10 mM diethanolamine pH 10.0 1 mM MgCl$_2$ and 0.5 mM CSPD (Tropix Inc. Boston, USA) ) and incubated for 20 min at 37° C. before measurement in a microplate luminometer (Luminoskan; Labsystems, Finland) with integral measurement for 1 second. The ALP activity of ERE-reporter alone was set at 1.

5. Ligand Binding Characteristics and Transactivation Function of Clone 29 Protein:

On the basis of the described high homology between clone 29 protein and rat ERα in the DBD and LBD it was hypothesized that clone 29 protein might encode a novel ER. Furthermore, biological effects of estrogens on rat prostate and ovary, which show high expression of clone 29 RNA, are well known (Griffiths, K., Davies, P., Eaton, C. I., Harper, M. E., Turkes, A., & Peeling W. B. (1991) in *Endocrine Dependent Tumours*, eds Voigt, K-D. & Knabbe, C. (Raven Press), pp 83–125; Richards, J. S (1994) *Endocrine Rev.* 15, 725–745; and Habenicht, U-F., Tunn, U. W., Senge, Th., Schroder, R. H., Schweikert, H. U., Bartsch, G., & El Etreby, M. F. (1993) *J. Steroid Biochem. Molec. Biol.* 44, 557–563). In order to analyze the steroid binding properties of clone 29 protein synthesized in vitro, the reticulocyte lysate was incubated at 8° C. for 16 h with increasing concentrations (0.3–6.0 nM) of [$^3$H]E2 in the presence or absence of a 200 fold molar excess of unlabelled E2. Linear transformation of saturation data-revealed a single population of binding sites for E2 with a $K_d$ (dissociation constant) of 0.6 nM (FIGS. 5A and C). Steroid binding specificity was measured by incubating reticulocyte lysate with 5 nM [$^3$H]E2 in the presence of 0.5, 50, 500 and 5,000 nM unlabelled competitors. Competition curves generated are indicative of an estrogen receptor in that only estrogens competed efficiently with [$^3$H]E2 for binding (FIG. 5B). Fifty percent inhibition of specific binding occured by 0.6 fold excess of unlabelled E2; diethylstilbestrol, estriol, estrone and 5α-androstane-3α,17β-diol were 5, 15, 50 and 150 times, respectively, less effective as competitors. Neither testosterone, progesterone, corticosterone nor 5α-androstane-3α,17β-diol were efficient competitors, even at the highest concentrations used (1000 fold excess). The dissociation constant and the steroid binding specificities measured are in good agreement with data previously reported for ERs in rat and human prostate, rat granulosa cells, rat antral follicles and whole rat ovarian tissue (Ekman, P., Barrack, E. R., Greene, G. L., Jensen, E. V., & Walsh. P. C (1983) *J. Clin. Endocrinol. Metab.* 57, 166–176; van Beurden-Lamers, W. M. O., Brinkmann, A. O., Mulder, E., & van der Molen, H. (1974) *Biochem. J* 140, 495–502; Kudolo, G. B., Elder, M. G., & Myatt, L. (1984) *J. Endocrinol.* 102, 83–91; and Kawashima, M., & Greenwald, G. S. (1993) *Biology of Reprod.* 48 172–179).

When clone 29 protein was labelled with a saturating dose of [$^3$H]E2 and analyzed on sucrose density gradients, a single peak of specifically bound radioactivity was observed. The sedimentation coefficient of this complex was about 7S, and it shifted to 4S in the presence of 0.4 M NaCl (not shown). To investigate the transcriptional regulatory properties of clone 29 protein, we performed co-transfection experiments in which CHO cells were transfected with a clone 29 protein expression vector and/or an estrogen-responsive reporter gene construct. Cells were incubated in the absence of E2 (clone 29) or in the presence of 100 nM E2 (Clone 29+E2) or in the presence of 100 nM E2 and 12 µM Tamoxifen (Clone 29+E2/Tam). In the absence of exogenously added E2 clone 29 protein showed considerable transcriptional activity which could be further increased by the addition of 100 nM E2 (FIG. 6). Simultaneous addition of a 10 fold excess of the antiestrogen Tamoxifen partially suppressed the E2 stimulated activity (FIG. 6). The constitutive transcriptional activity of clone 29 protein could be suppressed by the anti-estrogen ICI-1624384 (not shown). It has been shown previously that the wild-type mouse and human ERs are constitutive activators of transcription, and that the transcriptional activity can be stimulated further by the addition of E2 (Txukernan, M., Xiao-Kun Zhang., Hermann, T., Wills, K. N., Graupner, G., & Phal, M. (1990) *New Biologist* 2, 613–620 and Lees, J. A., Fawell, S. E., & Parker, M. G. (1989) *Nucl. Acids Res.* 17, 5477–5488). To obtain more insight into what concentrations of E2 effect clone 29 protein transcriptional activity, transient transfection experiments were carried out in the presence of increasing concentrations of E2. CHO-cells were transiently transfected with the ERE-reporter plasmid and the clone 29 protein expression plasmid. Cells were incubated with increasing concentrations of E2 (0.1–1000 nM), estrone (E1, 1000 nM), 5α-androstane-3β,17β-diol (3β-AD, 1000 nM) or no ligand added. Alkaline phosphatase activity (ALP) was measured as described and the activity in the absence of ligand (control) was set at 1. The figure shows relative ALP-activities (±SD) from three independent experiments. Clone 29 protein began to respond at 0.1 nM E2 and maximal stimulation was observed between 1 nm and 10 nM E2 (FIG. 7). The maximal stimulation factor was 2.6±0.5 fold (mean±SD. n=9) as compared to incubation in the absence of E2. Apart from E2 also estrone and 5α-androstane-3β, 17β-diol could stimulate transcriptional activity, albeit at higher concentrations (FIG. 7). Dexamethasone, testosterone, progesterone, 5α-androstane-3α,17β-diol, thyroid hormone and all-trans-retinoic acid could not stimulate transcriptional activity of clone 29 protein, even at the highest concentration (1000 nM) tested (not shown). The results of the co-transfection experiments are in agreement with the ligand binding and specificity data of clone 29 protein presented in FIG. 5. In control experiments, wild-type human ERα also showed transcriptional activity in the absence of E2, which could be increased by the addition of E2 (not shown).

6. Detection of Rat ER Expression by RT-PCR

The tissue specificity of expression of rat ERβ and ERα was determined using reverse transcriptase polymerase chain reaction (RT-PCR). The results of the experiment are shown in FIG. 8.

B. Isolation of Human Erβ

1. A human version of Erβ (hERβ) has also been cloned from human ovary. The tissue specificity of hERβ expression in a variety of cells was also determined using the RT-PCR technique. The results are shown in FIG. 9. It will be noticed that there is a very high level of mRNA of hERβ in human umbilical vein endothelial cells (HUVEC) but no detection of hERα in the same cells. In addition, it will be seen that in human osteosarcoma cell line (HOS-D4), hERβ is expressed in greater quantities compared to hERα.

I. A human version of ERβ (hERβ) has also been cloned. The tissue specificity of hERβ expression in a variety of cells was also determined using the RT-PCR technique. The results are shown in FIG. 9. It will be noticed that there is a very high level of mRNA of hERβ in human umbilical vein endothelial cells (HUVEC) but no detection of hERα in the same cells. In addition, it will be seen that in human osteosarcoma cell line (HOS-D4), hERβ is expressed in greater quantities compared to hERα.

The partial DNA sequence of hERβ is shown in FIG. 10 and a derived amino acid sequence is shown in FIG. 11.

Cloning of Human Erβ from Testis

A commercially available cDNA from human testis (Clontech, article no. HL1161x) was screened, using a fragment containing the ligand-binding domain of the rat Erβ cDNA as probe. Approximately $10^6$ recombinants were screened, resulting in one positive clone. Upon sequencing of this clone, it was seen that the insert was 1156 bp (FIGS. 13A and 13B). This corresponds to most of the translated region of a receptor with an overall homology of 90.0% to rat Erβ, therefore deduced to represent the human form of Erβ.

The cloned hERβ, however, lacks approximately 47 amino acids at the N-terminal end and 61 amino acids at the C-terminal end (as compared to the rat sequence). Further screening of the same library was unsuccessful. PCR technology was therefore used to obtain the remaining parts. For oligonucleotides were sunthesised; two degenerate oligonucleotides containing all possible codons for the amino acids adjacent to the initiation methionine and the stop codon, respectively, of the rat Erβ, and two specific oligonucleotides containing the sequence of the clone isolated from the human testis library and situated approximately 100 bp from respective end of this clone. PCR with the N-terminal and C-terminal pair of oligos yielded specific bands, that were subcloned and sequenced. The parts of these new clones that overlap the original cDNA clone are identical to this. It was thus possible to construct peptide and DNA sequences corresponding to the whole open reading frame (FIGS. 13A and 13B).

When comparing the human Erβ to rat Erβ, this receptor is 79.6% identical in the N-terminal domain, 98.5% in the DNA-binding domain, 85.6% in the hinge and 91.6% in the ligand-binding and F-domains. These numbers match very well those found when comparing the rat and human forms of Erα.

Studies of the expression of human Erβ using Northern blot show expression in testis and in ovaries. The expression in prostate, however, appears lower than found in the rat.

The human Erβ gene has been mapped to chromosome 14 using PCR and to region 14q22–23 using the FISH technique, whereas the human Erβ gene has been mapped to chromosome 6q25.

2. Comparison of ligand binding affinity of hERα and rERβ

The ligand affinity of the two estrogen receptors, human Erα (ovary) (hERβ) and rat Erβ (rERβ) was tested in binding saturation experiments and in binding competition experiments.

cDNA of the receptor subtypes hERα and rERβ were in vitro translated in rabbit reticulocyte lysate in presence of non-radioactive amino acids according to the instructions supplied by the manufacturer (Promega).

The radioactive ligand used in all experiments was 16α [$^{125}$I]-17β-estradiol ([$^{125}$I]-E2) (NEX-144, New England Nuclear). The method for the binding experiments was previously described in: Salomonsson M, Carlsson B, Haggblad J. *J. Steroid Biochem. Molec. Biol.* Vol. 50, No. 5/6 pp. 313–18, 1994. In brief, estrogen receptors are incubated with [$^{125}$I]-E2 to equilibrium (16–18 h at +4° C.). The incubation was stopped by separation of protein-bound

[$^{125}$I]-E2 from free [$^{125}$I]-E2 on Sephadex G25 columns. The radioactivity of the eluate is measured in a gamma-counter.

In the competition experiments, non-radioactive ligands were diluted in DMSO, mixed with [$^{125}$I]-E2 (approximately 100–200 pM), aliquoted in parallel, and finally hERα or rERβ was added. The final concentration of DMSO in the binding buffer was 2%.

The buffer used in the experiments was of the following composition: Hepes (pH=7.5) 20 mM, KCl 150 mM, EDTA 1 mM, glycerol (8.7%), monothioglycerol 6 mM, Na$_3$MO$_4$ 10 mM.

3. Equilibrium binding saturation experiments ($K_d$-determinations)

A range of concentrations of [$^{125}$I]-E2 were mixed with the ER:s and incubated as described above, free [$^{125}$I]-E2 was determined by substracting bound [$^{125}$I]-E2 from added [$^{125}$I]-E2. Binding data was analysed by Hill-plots and by Scatchard plots (FIG. 11). The equilibrium binding results are shown in Table 1. The apparent $K_d$-values for [$^{125}$I]-E2 differed between the two ER:s with approximately a factor of four; $K_d$(hERα):$K_d$(rERβ)=1:4.

TABLE 1

Equilibrium dissociation constants for [$^{125}$I]-E2 to the two subtypes.

| Receptor subtype | $K_d$ (Hill-plot) | $K_d$ (Scatchard-plot) |
|---|---|---|
| hERα | 0.06 nM | 0.09 nM |
| rERβ | 0.24 nM | 0.42 nM |

4. Competition experiments (IC$_{50}$ determinations)

The experiments were performed as described above. IC$_{50}$ values were obtained by applying a four parameter logistic analysis; $b=((b_{max}-b_{min})/(1+(I/IC_{50})^S))+b_{min}$, where I is the added concentration of binding inhibitor, IC$_{50}$ is the concentration of inhibitor at half maximal binding and S is a slope factor. The free concentration of [$^{125}$I]-E2 was determined by sampling an aliquot from the wells at the end of the incubation and then substract bound radioactivity from sampled total radioactivity.

Since the equilibrium binding experiments (above) showed that the $K_d$-values for [$^{125}$I]-E2 differed between the two ER:s, $K_i$-values (from the Cheng-Prusoff equation: $K_i=IC_{50}/(1+L/K_d)$ where L is free ([$^{125}$I]-E2]) were calculated for the compounds investigated. Two approaches for calculating RBA (Relative Binding Affinity) were used. The RBA values were derived using either the IC$_{50}$ values or the $K_i$ values. In both approaches, the value for the compound 16α-bromo-estradiol was selected as the reference value (100%). Both approaches gave similar results. The results are summarized in FIG. 12. In these Figures "4-OH-Tam"=4-hydroxy-tamoxifen; "DES"=diethylstilbestrol; "Hexestr"=hexestrol; "ICI-164384"=ICI plc compound no. 164382; "17β-E2"=17β-estradiol; "16a-B-E2"=16α-bromo-estradiol; "Ralox"=Raloxifen; and "17a-E2"=17α diol.

The results show that Erα and Erβ have significant different ligand binding affinities—the apparent $K_d$-values for [$^{125}$I]-E2 differed between the two ER's by a factor of about 4 ($K_d$(hERα): $K_d$(rERβ)≈1:4). Some compounds investigated showed significant differences in the competition for binding of [$^{125}$I]-E2 to the ER's. Certain compounds were found to be more potent inhibitors of [$^{125}$I]-E2 binding to hERα as compared to rERβ whereas others were found to be more potent inhibitors of [$^{125}$I]-E2 binding to rERβ than to hERα.

---

The invention claimed is:

1. An isolated polypeptide displaying the biological activity of ERβ, said polypeptide having more than about 95% amino acid sequence identity to the amino acid sequence of SEQ ID NO:2 or SEQ ID NO:5.

2. An isolated nucleic acid which codes for a polypeptide displaying the biological activity of ERβ, said polypeptide having more than about 95% amino acid sequence identity to the amino acid sequence of SEQ ID NO:2 or SEQ ID NO:5.

3. A recombinant DNA molecule, comprising a DNA sequence which codes for a polypeptide displaying the biological activity of ERβ, said polypeptide having the amino acid sequence of SEQ ID NO:2, SEQ ID NO:3, or SEQ ID NO:5.

4. A recombinant DNA molecule, comprising a DNA sequence which codes for a polypeptide displaying the biological activity of ERβ, said polypeptide having more than about 95% amino acid sequence identity to the amino acid sequence of SEQ ID NO:2 or SEQ ID NO:5.

5. An expression vector, comprising:
   (a) a nucleic acid which codes for a polypeptide displaying the biological activity of ERβ, said polypeptide having the amino acid sequence of SEQ ID NO:2, SEQ ID NO:3, or SEQ ID NO:5; and (b) a promoter sequence operably linked to said nucleic acid to allow expression of said nucleic acid and production of ERβ.

6. The expression vector of claim 5, wherein said nucleic acid comprises the nucleic acid sequence of SEQ ID NO:1.

7. The expression vector of claim 5, wherein said nucleic acid is clone 29.

8. The expression vector of claim 5, wherein said expression vector is pCMV29.

9. A method for producing ERβ, comprising the steps of:
(a) transforming or transfecting suitable host cells with a recombinant DNA molecule comprising a nucleic acid which codes for a polypeptide displaying the biological activity of ERβ, said polypeptide having the amino acid sequence of SEQ ID NO:2, SEQ ID NO:3, or SEQ ID NO:5; and
(b) culturing said host cells under conditions in which said cells express said nucleic acid and produce ERβ.

10. The method of claim 9, wherein said recombinant DNA molecule comprises a nucleic acid sequence which codes for a polypeptide displaying the biological activity of ERβ, said molecule being clone 29.

11. An isolated polypeptide displaying the biological activity of ERβ, said polypeptide having more than about 95% amino acid sequence identity to the amino acid sequence of SEQ ID NO:3, and wherein said isolated polypeptide is 485 amino acids in length.

12. An isolated nucleic acid which codes for a polypeptide displaying the biological activity of ERβ, said polypeptide having more than about 95% amino acid sequence identity to the amino acid sequence of SEQ ID NO:3, and wherein said polypeptide is 485 amino acids in length.

13. A recombinant DNA molecule, consisting of a DNA sequence which codes for a polypeptide displaying the biological activity of ERβ, said polypeptide having more than about 95% amino acid sequence identity to the amino acid sequence of SEQ ID NO:3, and wherein said polypeptide is 485 amino acids in length.

* * * * *

UNITED STATES PATENT AND TRADEMARK OFFICE
CERTIFICATE OF CORRECTION

| | | |
|---|---|---|
| PATENT NO. | : 7,132,261 B2 | Page 1 of 1 |
| APPLICATION NO. | : 10/278481 | |
| DATED | : November 7, 2006 | |
| INVENTOR(S) | : George Kuiper, Eva L. K. Enmark and Jan-Ake Gustafsson | |

It is certified that error appears in the above-identified patent and that said Letters Patent is hereby corrected as shown below:

(75) On the Title page of the Patent, under the section entitled: "Inventors", the first name of the first named inventor is incorrect. The correct first name of the inventor is --George-- not "Georg" - Kuiper.

Signed and Sealed this

Twentieth Day of March, 2007

JON W. DUDAS
*Director of the United States Patent and Trademark Office*

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 2568 base pairs
      (B) TYPE: nucleic acid
      (C) STRANDEDNESS: double
      (D) TOPOLOGY: linear (vi) ORIGINAL SOURCE:
      (A) ORGANISM: Rattus rattus (xi) SEQUENCE DESCRIPTION: SEQ ID NO: 1:

```
GGAATTCCGG GGGAGCTGGC CCAGGGGGAG CGGCTGGTGC TGCCACTGGC ATCCCTAGGC      60

ACCCAGGTCT GCAATAAAGT CTGGCAGCCA CTGCATGGCT GAGCGACAAC CAGTGGCTGG     120

GAGTCCGGCT CTGTGGCTGA GGAAAGCACC TGTCTGCATT TAGAGAATGC AAAATAGAGA     180

ATGTTTACCT GCCAGTCATT ACATCTGAGT CCCATGAGTC TCTGAGAACA TAATGTCCAT     240

CTGTACCTCT TCTCACAAGG AGTTTTCTCA GCTGCGACCC TCTGAAGACA TGGAGATCAA     300

AAACTCACCG TCGAGCCTTA GTTCCCTGCT TCCTATAACT GTAGCCAGTC CATCCTACCC     360

CTGGAGCACG GCCCCATCTA CATCCCTTCC TCCTACGTAG ACAACCGCCA TGAGTATTCA     420

GCTATGACAT TCTACAGTCC TGCTGTGATG AACTACAGTG TTCCCGGCAG CACCAGTAAC     480
```

```
CTGGACGGTG GGCCTGTCCG ACTGAGCACA AGCCCAAATG TGCTATGGCC AACTTCTGGG      540

CACCTGTCTC CTTTAGCGAC CCATTGCCAA TCATCGCTCC TCTATGCAGA ACCTCAAAAG      600

AGTCCTTGGT GTGAAGCAAG ATCACTAGAG CACACCTTAC CTGTAAACAG AGAGACACTG      660

AAGAGGAAGC TTAGTGGGAG CAGTTGTGCC AGCCCTGTTA CTAGTCCAAA CGCAAAGAGG      720

GATGCTCACT TCTGCCCCGT CTGCAGCGAT TATGCATCTG GTATCATTA CGGCGTTTGG       780

TCATGTGAAG GATGTAAGGC CTTTTTTAAA GAAGCATTC AAGGACATAA TGATTATATC       840

TGTCCAGCCA CGAATCAGTG TACCATAGAC AAGAACCGGC GTAAAAGCTG CCAGGCCTGC      900

CGACTTCGCA AGTGTTATGA AGTAGGAATG GTCAAGTGTG ATCCAGGAG AGAACGGTGT       960

GGGTACCGTA TAGTGCGGAG GCAGAGAAGT TCTAGCGAGC AGGTACACTG CCTGAGCAAA     1020

GCCAAGAGAA ACGGTGGGCA TGCACCCCGG GTGAAGGAGC TACTGCTGAG CACCTTGAGT     1080

CCAGAGCAAC TGGTGCTCAC CCTCCTGGAA GCTGAACCAC CCAATGTGCT GGTGAGCCGT     1140

CCCAGCATGC CCTTCACCGA GGCCTCCATG ATGATGTCCC TCACTAAGCT GGCGGACAAG     1200

GAACTGGTGC ACATGATTGG CTGGGCCAAG AAAATCCCTG GCTTTGTGGA GCTCAGCCTG     1260

TTGGACCAAG TCCGGCTCTT AGAAAGCTGC TGGATGGAGG TGCTAATGGT GGGACTGATG     1320

TGGCGCTCCA TCGACCACCC CGGCAAGCTC ATTTTCGCTC CCGACCTCGT TCTGGACAGG     1380

GATGAGGGGA AGTGCGTAGA AGGGATTCTG GAAATCTTTG ACATGCTCCT GGCGACGACG     1440

TCAAGGTTCC GTGAGTTAAA ACTCCAGCAC AAGGAGTATC TCTGTGTGAA GGCCATGATC     1500

CTCCTCAACT CCAGTATGTA CCCCTTGGCT TCTGCAAACC AGGAGGCAGA AAGTAGCCGG     1560

AAGCTGACAC ACCTACTGAA CGCGGTGACA GATGCCCTGG TCTGGGTGAT TGCGAAGAGT     1620

GGTATCTCCT CCCAGCAGCA GTCAGTCCGA CTGGCCAACC TCCTGATGCT TCTTTCTCAC     1680

GTCAGGCACA TCAGTAACAA GGGCATGGAA CATCTGCTCA GCATGAAGTG CAAAAATGTG     1740

GTCCCGGTGT ATGACCTGCT GCTGGAGATG CTGAATGCTC ACACGCTTCG AGGGTACAAG     1800

TCCTCAATCT CGGGGTCTGA GTGCAGCTCA ACAGAGGACA GTAAGAACAA AGAGAGCTCC     1860

CAGAACCTAC AGTCTCAGTG ATGGCCAGGC CTGAGGCGGA CAGACTACAG AGATGGTCAA     1920

AAGTGGAACA TGTACCCTAG CATCTGGGGG TTCCTCTTAG GGCTGCCTTG GTTACGCACC     1980

CCTTACCCAC ACTGCACTTC CCAGGAGTCA GGGTGGTTGT GTGGCGGTGT TCCTCATACC     2040

AGGATGTACC ACCGAATGCC AAGTTCTAAC TTGTATAGCC TTGAAGGCTC TCGGTGTACT     2100

TACTTTCTGT CTCCTTGCCC ACTTGGAAAC ATCTGAAAGG TTCTGGAACT AAAGGTCAAA     2160

GTCTGATTTG GAAGGATTGT CCTTAGTCAG GAAAAGGAAT ATGGCATGTG ACACAGCTAT     2220

AAGAAATGGA CTGTAGGACT GTGTGGCCAT AAAATCAACC TTTGGATGGC GTCTTCTAGA     2280

CCACTTGATT GTAGGATTGA AAACCACATT GACAATCAGC TCATTTCGCA TTCCTGCCTC     2340

ACGGGTCTGT GAGGACTCAT TAATGTCATG GGTTATTCTA TCAAAGACCA GAAAGATAGT     2400

GCAAGCTTAG ATGTACCTTG TTCCTCCTCC CAGACCCTTG GGTTACATCC TTAGAGCCTG     2460

CTTATTTGGT CTGTCTGAAT GTGGTCATTG TCATGGGTTA AGATTTAAAT CTCTTTGTAA     2520

TATTGGCTTC CTTGAAGCTA TGTCATCTTT CTCTCTCTCC CGGAATTC                  2568
```

(2) INFORMATION FOR SEQ ID NO: 2:

(i) SEQUENCE CHARACTERISTICS:
        (A) LENGTH: 485 amino acids
        (B) TYPE: amino acid
        (D) TOPOLOGY: linear (vi) ORIGINAL SOURCE:
    (A) ORGANISM: Rattus rattus (xi) SEQUENCE DESCRIPTION: SEQ ID NO: 2:

```
Met Thr Phe Tyr Ser Pro Ala Val Met Asn Tyr Ser Val Pro Gly Ser
1               5                   10                  15

Thr Ser Asn Leu Asp Gly Gly Pro Val Arg Leu Ser Thr Ser Pro Asn
            20                  25                  30

Val Leu Trp Pro Thr Ser Gly His Leu Ser Pro Leu Ala Thr His Cys
            35                  40                  45

Gln Ser Ser Leu Leu Tyr Ala Glu Pro Gln Lys Ser Pro Trp Cys Glu
50                      55                  60

Ala Arg Ser Leu Glu His Thr Leu Pro Val Asn Arg Glu Thr Leu Lys
65                  70                  75                  80

Arg Lys Leu Ser Gly Ser Ser Cys Ala Ser Pro Val Thr Ser Pro Asn
                85                  90                  95

Ala Lys Arg Asp Ala His Phe Cys Pro Val Cys Ser Asp Tyr Ala Ser
            100                 105                 110

Gly Tyr His Tyr Gly Val Trp Ser Cys Glu Gly Cys Lys Ala Phe Phe
            115                 120                 125

Lys Arg Ser Ile Gln Gly His Asn Asp Tyr Ile Cys Pro Ala Thr Asn
130                 135                 140

Gln Cys Thr Ile Asp Lys Asn Arg Arg Lys Ser Cys Gln Ala Cys Arg
145                 150                 155                 160

Leu Arg Lys Cys Tyr Glu Val Gly Met Val Lys Cys Gly Ser Arg Arg
                165                 170                 175

Glu Arg Cys Gly Tyr Arg Ile Val Arg Arg Gln Arg Ser Ser Ser Glu
            180                 185                 190

Gln Val His Cys Leu Ser Lys Ala Lys Arg Asn Gly Gly His Ala Pro
            195                 200                 205

Arg Val Lys Glu Leu Leu Leu Ser Thr Leu Ser Pro Glu Gln Leu Val
        210                 215                 220

Leu Thr Leu Leu Glu Ala Glu Pro Pro Asn Val Leu Val Ser Arg Pro
225                 230                 235                 240

Ser Met Pro Phe Thr Glu Ala Ser Met Met Met Ser Leu Thr Lys Leu
                245                 250                 255

Ala Asp Lys Glu Leu Val His Met Ile Gly Trp Ala Lys Lys Ile Pro
            260                 265                 270

Gly Phe Val Glu Leu Ser Leu Leu Asp Gln Val Arg Leu Leu Glu Ser
            275                 280                 285

Cys Trp Met Glu Val Leu Met Val Gly Leu Met Trp Arg Ser Ile Asp
290                 295                 300

His Pro Gly Lys Leu Ile Phe Ala Pro Asp Leu Val Leu Asp Arg Asp
305                 310                 315                 320

Glu Gly Lys Cys Val Glu Gly Ile Leu Glu Ile Phe Asp Met Leu Leu
                325                 330                 335

Ala Thr Thr Ser Arg Phe Arg Glu Leu Lys Leu Gln His Lys Glu Tyr
            340                 345                 350

Leu Cys Val Lys Ala Met Ile Leu Leu Asn Ser Ser Met Tyr Pro Leu
            355                 360                 365

Ala Ser Ala Asn Gln Glu Ala Glu Ser Ser Arg Lys Leu Thr His Leu
370                 375                 380

Leu Asn Ala Val Thr Asp Ala Leu Val Trp Val Ile Ala Lys Ser Gly
385                 390                 395                 400
```

```
Ile Ser Ser Gln Gln Gln Ser Val Arg Leu Ala Asn Leu Leu Met Leu
                405                 410                 415

Leu Ser His Val Arg His Ile Ser Asn Lys Gly Met Glu His Leu Leu
                420                 425                 430

Ser Met Lys Cys Lys Asn Val Val Pro Val Tyr Asp Leu Leu Leu Glu
                435                 440                 445

Met Leu Asn Ala His Thr Leu Arg Gly Tyr Lys Ser Ser Ile Ser Gly
                450                 455                 460

Ser Glu Cys Ser Ser Thr Glu Asp Ser Lys Asn Lys Glu Ser Ser Gln
465                 470                 475                 480

Asn Leu Gln Ser Gln
                485

(2) INFORMATION FOR SEQ ID NO: 3:

(i) SEQUENCE CHARACTERISTICS:
        (A) LENGTH: 485 amino acids
        (B) TYPE: amino acid
        (D) TOPOLOGY: linear (vi) ORIGINAL SOURCE:
        (A) ORGANISM: Homo sapiens (xi) SEQUENCE DESCRIPTION: SEQ ID NO: 3:

Met Thr Phe Tyr Ser Pro Ala Val Met Asn Tyr Ser Ile Pro Ser Asn
1               5                   10                  15

Val Thr Asn Leu Glu Gly Gly Pro Gly Arg Gln Thr Thr Ser Pro Asn
                20                  25                  30

Val Leu Trp Pro Thr Pro Gly His Leu Ser Pro Leu Val Val His Arg
                35                  40                  45

Gln Leu Ser His Leu Tyr Ala Glu Pro Gln Lys Ser Pro Trp Cys Glu
                50                  55                  60

Ala Arg Ser Leu Glu His Thr Leu Pro Val Asn Arg Glu Thr Leu Lys
65                  70                  75                  80

Arg Lys Val Ser Gly Asn Arg Cys Ala Ser Pro Val Thr Gly Pro Gly
                85                  90                  95

Ser Lys Arg Asp Ala His Phe Cys Ala Val Cys Ser Asp Tyr Ala Ser
                100                 105                 110

Gly Tyr His Tyr Gly Val Trp Ser Cys Glu Gly Cys Lys Ala Phe Phe
                115                 120                 125

Lys Arg Ser Ile Gln Gly His Asn Asp Tyr Ile Cys Pro Ala Thr Asn
                130                 135                 140

Gln Cys Thr Ile Asp Lys Asn Arg Arg Lys Ser Cys Gln Ala Cys Arg
145                 150                 155                 160

Leu Arg Lys Cys Tyr Glu Val Gly Met Val Lys Cys Gly Ser Arg Arg
                165                 170                 175

Glu Arg Cys Gly Tyr Arg Leu Val Arg Arg Gln Arg Ser Ala Asp Glu
                180                 185                 190

Gln Leu His Cys Ala Gly Lys Ala Lys Arg Ser Gly Gly His Ala Pro
                195                 200                 205

Arg Val Arg Glu Leu Leu Leu Asp Ala Leu Ser Pro Glu Gln Leu Val
                210                 215                 220

Leu Thr Leu Leu Glu Ala Glu Pro Pro His Val Leu Ile Ser Arg Pro
225                 230                 235                 240

Ser Ala Pro Phe Thr Glu Ala Ser Met Met Met Ser Leu Thr Lys Leu
                245                 250                 255
```

```
Ala Asp Lys Glu Leu Val His Met Ile Ser Trp Ala Lys Lys Ile Pro
            260                 265                 270

Gly Phe Val Glu Leu Ser Leu Phe Asp Gln Val Arg Leu Leu Glu Ser
            275                 280                 285

Cys Trp Met Glu Val Leu Met Met Gly Leu Met Trp Arg Ser Ile Asp
            290                 295                 300

His Pro Gly Lys Leu Ile Phe Ala Pro Asp Leu Val Leu Asp Arg Asp
305                 310                 315                 320

Glu Gly Lys Cys Val Glu Gly Ile Leu Glu Ile Phe Asp Met Leu Leu
                325                 330                 335

Ala Thr Thr Ser Arg Phe Arg Glu Leu Lys Leu Gln His Lys Glu Tyr
            340                 345                 350

Leu Cys Val Lys Ala Met Ile Leu Leu Asn Ser Ser Met Tyr Pro Leu
            355                 360                 365

Val Thr Ala Thr Gln Asp Ala Asp Ser Ser Arg Lys Leu Ala His Leu
            370                 375                 380

Leu Asn Ala Val Thr Asp Ala Leu Val Trp Val Ile Ala Lys Ser Gly
385                 390                 395                 400

Ile Ser Ser Gln Gln Gln Ser Met Arg Leu Ala Asn Leu Leu Met Leu
                405                 410                 415

Leu Ser His Val Arg His Ala Ser Asn Lys Gly Met Glu His Leu Leu
            420                 425                 430

Asn Met Lys Cys Lys Asn Val Val Pro Val Tyr Asp Leu Leu Leu Glu
            435                 440                 445

Met Leu Asn Ala His Val Leu Arg Gly Cys Lys Ser Ser Ile Thr Gly
450                 455                 460

Ser Glu Cys Ser Pro Ala Glu Asp Ser Lys Ser Lys Glu Gly Ser Gln
465                 470                 475                 480

Asn Leu Gln Ser Gln
            485

(2) INFORMATION FOR SEQ ID NO: 4:

(i) SEQUENCE CHARACTERISTICS:
        (A) LENGTH: 1460 base pairs
        (B) TYPE: nucleic acid
        (C) STRANDEDNESS: double
        (D) TOPOLOGY: linear (vi) ORIGINAL SOURCE:
        (A) ORGANISM: Homo sapiens (xi) SEQUENCE DESCRIPTION: SEQ ID NO: 4:

CTATGACATT CTACAGTCCT GCTGTGATGA ATTACAGCAT TCCCAGCAAT GTCACTAACT      60

TGGAAGGTGG GCCTGGTCGG CAGACCACAA GCCCAAATGT GTTGTGGCCA ACACCTGGGC     120

ACCTTTCTCC TTTAGTGGTC CATCGCCAGT TATCACATCT GTATGCGGAA CCTCAAAAGA    180

GTCCCTGGTG TGAAGCAAGA TCGCTAGAAC ACACCTTACC TGTAAACAGA GAGACACTGA    240

AAAGGAAGGT TAGTGGGAAC CGTTGCGCCA GCCCTGTTAC TGGTCCAGGT TCAAAGAGGG    300

ATGCTCACTT CTGCGCTGTC TGCAGCGATT ACGCATCGGG ATATCACTAT GGAGTCTGGT    360

CGTGTGAAGG ATGTAAGGCC TTTTTTAAAA GAAGCATTCA AGGACATAAT GATTATATTT    420

GTCCAGCTAC AAATCAGTGT ACAATCGATA AAAACCGGCG CAAGAGCTGC CAGGCCTGCC    480

GACTTCGGAA GTGTTACGAA GTGGGAATGG TGAAGTGTGG CTCCCGGAGA GAGAGATGTG    540

GGTACCGCCT TGTGCGGAGA CAGAGAAGTG CCGACGAGCA GCTGCACTGT GCCGGCAAGG    600
```

-continued

```
CCAAGAGAAG TGGCGGCCAC GCGCCCCGAG TGCGGGAGCT GCTGCTGGAC GCCCTGAGCC      660

CCGAGCAGCT AGTGCTCACC CTCCTGGAGG CTGAGCCGCC CCATGTGCTG ATCAGCCGCC      720

CCAGTGCGCC CTTCACCGAG GCCTCCATGA TGATGTCCCT GACCAAGTTG GCCGACAAGG      780

AGTTGGTACA CATGATCAGC TGGGCCAAGA AGATTCCCGG CTTTGTGGAG CTCAGCCTGT      840

TCGACCAAGT GCGGCTCTTG GAGAGCTGTT GGATGGAGGT GTTAATGATG GGGCTGATGT      900

GGCGCTCAAT TGACCACCCC GGCAAGCTCA TCTTTGCTCC AGATCTTGTT CTGGACAGGG      960

ATGAGGGGAA ATGCGTAGAA GGAATTCTGG AAATCTTTGA CATGCTCCTG GCAACTACTT     1020

CAAGGTTTCG AGAGTTAAAA CTCCAACACA AGAATATCT CTGTGTCAAG GCCATGATCC      1080

TGCTCAATTC CAGTATGTAC CCTCTGGTCA CAGCGACCCA GGATGCTGAC AGCAGCCGGA     1140

AGCTGGCTCA CTTGCTGAAC GCCGTGACCG ATGCTTTGGT TTGGGTGATT GCCAAGAGCG     1200

GCATCTCCTC CCAGCAGCAA TCCATGCGCC TGGCTAACCT CCTGATGCTC CTGTCCCACG     1260

TCAGGCATGC GAGTAACAAG GGCATGGAAC ATCTGCTCAA CATGAAGTGC AAAAATGTGG     1320

TCCCAGTGTA TGACCTGCTG CTGGAGATGC TGAATGCCCA CGTGCTTCGC GGGTGCAAGT     1380

CCTCCATCAC GGGGTCCGAG TGCAGCCCGG CAGAGGACAG TAAAAGCAAA GAGGGCTCCC     1440

AGAACCTACA GTCTCAGTGA                                                  1460
```

(2) INFORMATION FOR SEQ ID NO: 5:

(i) SEQUENCE CHARACTERISTICS:
        (A) LENGTH: 485 amino acids
        (B) TYPE: amino acid
        (D) TOPOLOGY: linear (vi) ORIGINAL SOURCE:
        (A) ORGANISM: Mus musculus (xi) SEQUENCE DESCRIPTION: SEQ ID NO: 5:

```
Met Ala Phe Tyr Ser Pro Ala Val Met Asn Tyr Ser Val Pro Ser Ser
1               5                   10                  15

Thr Gly Asn Leu Glu Gly Gly Pro Val Arg Gln Thr Ala Ser Pro Asn
            20                  25                  30

Val Leu Trp Pro Thr Ser Gly His Leu Ser Pro Leu Ala Thr His Cys
        35                  40                  45

Gln Ser Ser Leu Leu Tyr Ala Glu Pro Gln Lys Ser Pro Trp Cys Glu
    50                  55                  60

Ala Arg Ser Leu Glu His Thr Leu Pro Val Asn Arg Glu Thr Leu Lys
65                  70                  75                  80

Arg Lys Leu Gly Gly Ser Gly Cys Ala Ser Pro Val Thr Ser Pro Ser
                85                  90                  95

Thr Lys Arg Asp Ala His Phe Cys Ala Val Cys Ser Asp Tyr Ala Ser
            100                 105                 110

Gly Tyr His Tyr Gly Val Trp Ser Cys Glu Gly Cys Lys Ala Phe Phe
        115                 120                 125

Lys Arg Ser Ile Gln Gly His Asn Asp Tyr Ile Cys Pro Ala Thr Asn
    130                 135                 140

Gln Cys Thr Ile Asp Lys Asn Arg Arg Lys Asn Cys Gln Ala Cys Arg
145                 150                 155                 160

Leu Arg Lys Cys Tyr Glu Val Gly Met Val Lys Cys Gly Ser Arg Arg
                165                 170                 175

Glu Arg Cys Gly Tyr Arg Ile Val Arg Arg Gln Arg Ser Ala Ser Glu
            180                 185                 190
```

```
Gln Val His Cys Leu Asn Lys Ala Lys Arg Thr Ser Gly His Thr Pro
        195                 200                 205

Arg Val Lys Glu Leu Leu Asn Ser Leu Ser Pro Glu Gln Leu Val
    210                 215                 220

Leu Thr Leu Leu Glu Ala Glu Pro Pro Asn Val Leu Val Ser Arg Pro
225                 230                 235                 240

Ser Met Pro Phe Thr Glu Ala Ser Met Met Ser Leu Thr Lys Leu
                245                 250                 255

Ala Asp Lys Glu Leu Val His Met Ile Gly Trp Ala Lys Lys Ile Pro
            260                 265                 270

Gly Phe Val Glu Leu Ser Leu Leu Asp Gln Val Arg Leu Leu Glu Ser
            275                 280                 285

Cys Trp Met Glu Val Leu Met Val Gly Leu Met Trp Arg Ser Ile Asp
290                 295                 300

His Pro Gly Lys Leu Ile Phe Ala Pro Asp Leu Val Leu Asp Arg Asp
305                 310                 315                 320

Glu Gly Lys Cys Val Glu Gly Ile Leu Glu Ile Phe Asp Met Leu Leu
                325                 330                 335

Ala Thr Thr Ala Arg Phe Arg Glu Leu Lys Leu Gln His Lys Glu Tyr
                340                 345                 350

Leu Cys Val Lys Ala Met Ile Leu Leu Asn Ser Ser Met Tyr His Leu
            355                 360                 365

Ala Thr Ala Ser Gln Glu Ala Glu Ser Ser Arg Lys Leu Thr His Leu
            370                 375                 380

Leu Asn Ala Val Thr Asp Ala Leu Val Trp Val Ile Ser Lys Ser Arg
385                 390                 395                 400

Ile Ser Ser Gln Gln Gln Ser Val Arg Leu Ala Asn Leu Leu Met Leu
                405                 410                 415

Leu Ser His Val Arg His Ile Ser Asn Lys Gly Met Glu His Leu Leu
            420                 425                 430

Ser Met Lys Cys Lys Asn Val Val Pro Val Tyr Asp Leu Leu Leu Glu
            435                 440                 445

Met Leu Asn Ala His Thr Leu Arg Gly Tyr Lys Ser Ser Ile Ser Gly
450                 455                 460

Ser Gly Cys Cys Ser Thr Glu Asp Ser Lys Ser Lys Glu Gly Ser Gln
465                 470                 475                 480

Asn Leu Gln Ser Gln
                485

(2) INFORMATION FOR SEQ ID NO: 6:

(i) SEQUENCE CHARACTERISTICS:
        (A) LENGTH: 1458 base pairs
        (B) TYPE: nucleic acid
        (C) STRANDEDNESS: double
        (D) TOPOLOGY: linear (vi) ORIGINAL SOURCE:
        (A) ORGANISM: Mus musculus (xi) SEQUENCE DESCRIPTION: SEQ ID NO: 6:

ATGGCATTCT ACAGTCCTGC TGTGATGAAC TACAGTGTTC CCAGCAGCAC CGGTAACCTG      60

GAAGGTGGGC CTGTTCGCCA GACTGCAAGC CCAAATGTGC TATGGCCAAC TTCTGGACAC    120

CTCTCTCCTT TAGCCACCCA CTGCCAATCA TCGCTTCTCT ATGCAGAACC TCAAAAGAGT    180

CCTTGGTGTG AAGCAAGATC ACTAGAACAC ACCTTGCCTG TAAACAGAGA GACCCTGAAG    240
```

```
AGGAAGCTTG GCGGGAGCGG TTGTGCCAGC CCTGTTACTA GTCCAAGCAC CAAGAGGGAT      300

GCTCACTTCT GTGCCGTCTG CAGTGATTAT GCATCTGGGT ATCATTACGG TGTCTGGTCC      360

TGTGAAGGAT GTAAGGCCTT TTTTAAAAGA AGCATTCAAG GACATAATGA CTATATCTGT      420

CCAGCCACGA ATCAGTGTAC GATAGACAAG AACCGGCGTA AAAACTGCCA GGCCTGCCGA      480

CTTCGCAAGT GTTACGAAGT AGGAATGGTC AAGTGTGGAT CCAGGAGAGA AAGGTGTGGG      540

TACCGAATAG TACGAAGACA GAGAAGTGCC AGCGAGCAGG TGCATTGCCT GAACAAAGCC      600

AAGAGAACCA GTGGGCACAC ACCCCGGGTG AAGGAGCTAC TGCTGAACTC TCTGAGTCCC      660

GAGCAGCTGG TGCTCACCCT GCTGGAAGCT GAGCCACCCA ATGTGCTAGT GAGTCGTCCC      720

AGCATGCCCT TCACCGAGGC CTCCATGATG ATGTCCCTTA CGAAGCTGGC TGACAAGGAA      780

CTGGTGCACA TGATTGGCTG GCCAAGAAAA ATCCCTGGCT TTGTGGAGCT CAGCCTGTTG      840

GACCAAGTCC GCCTCTTGGA AAGCTGCTGG ATGGAGGTGC TGATGGTGGG GCTGATGTGG      900

CGCTCCATCG ACCACCCCGG CAAGCTCATC TTTGCTCCAG ACCTCGTTCT GGACAGGGAT      960

GAGGGGAAGT GCGTGGAAGG GATTCTGGAA ATCTTTGACA TGCTCCTGGC GACGACGGCA     1020

CGGTTCCGTG AGTTAAAACT GCAGCACAAA GAATATCTGT GTGTGAAGGC CATGATTCTC     1080

CTCAACTCCA GTATGTACCA CTTGGCTACC GCAAGCCAGG AAGCAGAGAG TAGCCGGAAG     1140

CTGACACACC TATTGAACGC AGTGACAGAT GCCCTGGTCT GGGTGATTTC GAAGAGTAGA     1200

ATCTCTTCCC AGCAGCAGTC AGTCCGTCTG GCCAACCTCC TGATGCTTCT TTCTCATGTC     1260

AGGCACATCA GTAACAAGGG CATGGAACAT CTGCTCAGCA TGAAGTGCAA AAATGTGGTC     1320

CCGGTGTACG ACCTGCTGCT GGAGATGCTG AATGCTCACA CGCTTCGAGG GTACAAGTCC     1380

TCAATCTCGG GGTCTGGGTG CTGCTCGACA GAGGACAGTA AGAGCAAAGA GGGCTCCCAG     1440

AACCTCCAGT CTCAGTGA                                                  1458

(2) INFORMATION FOR SEQ ID NO: 7:

(i) SEQUENCE CHARACTERISTICS:
        (A) LENGTH: 226 amino acids
        (B) TYPE: amino acid
        (D) TOPOLOGY: linear (vi) ORIGINAL SOURCE:
        (A) ORGANISM: Rattus rattus (xi) SEQUENCE DESCRIPTION: SEQ ID NO: 7:

Glu Leu Val His Met Ile Gly Trp Ala Lys Lys Ile Pro Gly Phe Val
1               5                  10                  15

Glu Leu Ser Leu Leu Asp Gln Val Arg Leu Leu Glu Ser Cys Trp Met
            20                  25                  30

Glu Val Leu Met Val Gly Leu Met Trp Arg Ser Ile Asp His Pro Gly
        35                  40                  45

Lys Leu Ile Phe Ala Pro Asp Leu Val Leu Asp Arg Asp Glu Gly Lys
    50                  55                  60

Cys Val Glu Gly Ile Leu Glu Ile Phe Asp Met Leu Leu Ala Thr Thr
65                  70                  75                  80

Ser Arg Phe Arg Glu Leu Lys Leu Gln His Lys Glu Tyr Leu Cys Val
                85                  90                  95

Lys Ala Met Ile Leu Leu Asn Ser Ser Met Tyr Pro Leu Ala Ser Ala
            100                 105                 110

Asn Gln Glu Ala Glu Ser Ser Arg Lys Leu Thr His Leu Leu Asn Ala
        115                 120                 125
```

```
Val Thr Asp Ala Leu Val Trp Val Ile Ala Lys Ser Gly Ile Ser Ser
    130                 135                 140

Gln Gln Gln Ser Val Arg Leu Ala Asn Leu Leu Met Leu Leu Ser His
145                 150                 155                 160

Val Arg His Ile Ser Asn Lys Gly Met Glu His Leu Leu Ser Met Lys
                165                 170                 175

Cys Lys Asn Val Val Pro Val Tyr Asp Leu Leu Leu Glu Met Leu Asn
            180                 185                 190

Ala His Thr Leu Arg Gly Tyr Lys Ser Ser Ile Ser Gly Ser Glu Cys
        195                 200                 205

Ser Ser Thr Glu Asp Ser Lys Asn Lys Glu Ser Ser Gln Asn Leu Gln
    210                 215                 220

Ser Gln
225

(2) INFORMATION FOR SEQ ID NO: 8:

(i) SEQUENCE CHARACTERISTICS:
        (A) LENGTH: 243 amino acids
        (B) TYPE: amino acid
        (D) TOPOLOGY: linear (vi) ORIGINAL SOURCE:
        (A) ORGANISM: Rattus rattus (xi) SEQUENCE DESCRIPTION: SEQ ID NO: 8:

Glu Leu Val His Met Ile Asn Trp Ala Lys Arg Val Pro Gly Phe Gly
1               5                   10                  15

Asp Leu Asn Leu His Asp Gln Val His Leu Leu Glu Cys Ala Trp Leu
            20                  25                  30

Glu Ile Leu Met Ile Gly Leu Val Trp Arg Ser Met Glu His Pro Gly
        35                  40                  45

Lys Leu Leu Phe Ala Pro Asn Leu Leu Leu Asp Arg Asn Gln Gly Lys
    50                  55                  60

Cys Val Glu Gly Met Val Glu Ile Phe Asp Met Leu Leu Ala Thr Ser
65                  70                  75                  80

Ser Arg Phe Arg Met Met Asn Leu Gln Gly Glu Glu Phe Val Cys Leu
                85                  90                  95

Lys Ser Ile Ile Leu Leu Asn Ser Gly Val Tyr Thr Phe Leu Ser Ser
            100                 105                 110

Thr Leu Lys Ser Leu Glu Glu Lys Asp His Ile His Arg Val Leu Asp
        115                 120                 125

Lys Ile Asn Asp Thr Leu Ile His Leu Met Ala Lys Ala Gly Leu Thr
    130                 135                 140

Leu Gln Gln Gln His Arg Arg Leu Ala Gln Leu Leu Leu Ile Leu Ser
145                 150                 155                 160

His Ile Arg His Met Ser Asn Lys Gly Met Glu His Leu Tyr Asn Met
                165                 170                 175

Lys Cys Lys Asn Val Val Pro Leu Tyr Asp Leu Leu Leu Glu Met Leu
            180                 185                 190

Asp Ala His Arg Leu His Ala Pro Ala Ser Arg Met Gly Val Pro Pro
        195                 200                 205

Glu Glu Pro Ser Gln Ser Gln Leu Thr Thr Thr Ser Ser Thr Ser Ala
    210                 215                 220

His Ser Leu Gln Thr Tyr Tyr Ile Pro Pro Glu Ala Glu Gly Phe Pro
225                 230                 235                 240
```

Asn Thr Ile (2) INFORMATION FOR SEQ ID NO: 9:

(i) SEQUENCE CHARACTERISTICS:
        (A) LENGTH: 243 amino acids
        (B) TYPE: amino acid
        (D) TOPOLOGY: linear (vi) ORIGINAL SOURCE:
        (A) ORGANISM: Mus musculus (xi) SEQUENCE DESCRIPTION: SEQ ID NO: 9:

```
Glu Leu Val His Met Ile Asn Trp Ala Lys Arg Val Pro Gly Phe Gly
1               5                   10                  15

Asp Leu Asn Leu His Asp Gln Val His Leu Glu Cys Ala Trp Leu
            20                  25                  30

Glu Ile Leu Met Ile Gly Leu Val Trp Arg Ser Met Glu His Pro Gly
            35                  40                  45

Lys Leu Leu Phe Ala Pro Asn Leu Leu Leu Asp Arg Asn Gln Gly Lys
 50                  55                  60

Cys Val Glu Gly Met Val Glu Ile Phe Asp Met Leu Leu Ala Thr Ser
 65                  70                  75                  80

Ser Arg Phe Arg Met Met Asn Leu Gln Gly Glu Glu Phe Val Cys Leu
                85                  90                  95

Lys Ser Ile Ile Leu Leu Asn Ser Gly Val Tyr Thr Phe Leu Ser Ser
            100                 105                 110

Thr Leu Lys Ser Leu Glu Glu Lys Asp His Ile His Arg Val Leu Asp
            115                 120                 125

Lys Ile Thr Asp Thr Leu Ile His Leu Met Ala Lys Ala Gly Leu Thr
 130                 135                 140

Leu Gln Gln Gln His Arg Arg Leu Ala Gln Leu Leu Leu Ile Leu Ser
145                 150                 155                 160

His Ile Arg His Met Ser Asn Lys Gly Met Glu His Leu Tyr Asn Met
                165                 170                 175

Lys Cys Lys Asn Val Val Pro Leu Tyr Asp Leu Leu Leu Glu Met Leu
            180                 185                 190

Asp Ala His Arg Leu His Ala Pro Ala Ser Arg Met Gly Val Pro Pro
            195                 200                 205

Glu Glu Pro Ser Gln Thr Gln Leu Ala Thr Thr Ser Ser Thr Ser Ala
 210                 215                 220

His Ser Leu Gln Thr Tyr Tyr Ile Pro Pro Glu Ala Glu Gly Phe Pro
225                 230                 235                 240

Asn Thr Ile
```

(2) INFORMATION FOR SEQ ID NO: 10:

(i) SEQUENCE CHARACTERISTICS:
        (A) LENGTH: 243 amino acids
        (B) TYPE: amino acid
        (D) TOPOLOGY: linear (vi) ORIGINAL SOURCE:
        (A) ORGANISM: Homo sapiens (xi) SEQUENCE DESCRIPTION: SEQ ID NO: 10:

```
Glu Leu Val His Met Ile Asn Trp Ala Lys Arg Val Pro Gly Phe Val
1               5                   10                  15
```

```
Asp Leu Thr Leu His Asp Gln Val His Leu Glu Cys Ala Trp Leu
            20              25              30

Glu Ile Leu Met Ile Gly Leu Val Trp Arg Ser Met Glu His Pro Val
            35              40              45

Lys Leu Leu Phe Ala Pro Asn Leu Leu Leu Asp Arg Asn Gln Gly Lys
 50              55              60

Cys Val Glu Gly Met Val Glu Ile Phe Asp Met Leu Leu Ala Thr Ser
 65              70              75              80

Ser Arg Phe Arg Met Met Asn Leu Gln Gly Glu Glu Phe Val Cys Leu
                85              90              95

Lys Ser Ile Ile Leu Leu Asn Ser Gly Val Tyr Thr Phe Leu Ser Ser
            100             105             110

Thr Leu Lys Ser Leu Glu Glu Lys Asp His Ile His Arg Val Leu Asp
            115             120             125

Lys Ile Thr Asp Thr Leu Ile His Leu Met Ala Lys Ala Gly Leu Thr
130             135             140

Leu Gln Gln Gln His Gln Arg Leu Ala Gln Leu Leu Leu Ile Leu Ser
145             150             155             160

His Ile Arg His Met Ser Asn Lys Gly Met Glu His Leu Tyr Ser Met
            165             170             175

Lys Cys Lys Asn Val Val Pro Leu Tyr Asp Leu Leu Leu Glu Met Leu
            180             185             190

Asp Ala His Arg Leu His Ala Pro Thr Ser Arg Gly Gly Ala Ser Val
            195             200             205

Glu Glu Thr Asp Gln Ser His Leu Ala Thr Ala Gly Ser Thr Ser Ser
            210             215             220

His Ser Leu Gln Lys Tyr Tyr Ile Thr Gly Glu Ala Glu Gly Phe Pro
225             230             235             240

Ala Thr Val (2) INFORMATION FOR SEQ ID NO: 11:

(i) SEQUENCE CHARACTERISTICS:
        (A) LENGTH: 66 amino acids
        (B) TYPE: amino acid
        (D) TOPOLOGY: linear (vi) ORIGINAL SOURCE:
        (A) ORGANISM: Rattus rattus (xi) SEQUENCE DESCRIPTION: SEQ ID NO: 11:

Cys Pro Val Cys Ser Asp Tyr Ala Ser Gly Tyr His Tyr Gly Val Trp
1               5              10              15

Ser Cys Glu Gly Cys Lys Ala Phe Phe Lys Arg Ser Ile Gln Gly His
            20              25              30

Asn Asp Tyr Ile Cys Pro Ala Thr Asn Gln Cys Thr Ile Asp Lys Asn
            35              40              45

Arg Arg Lys Ser Cys Gln Ala Cys Arg Leu Arg Lys Cys Tyr Glu Val
         50              55              60

Gly Met
65

(2) INFORMATION FOR SEQ ID NO: 12:

(i) SEQUENCE CHARACTERISTICS:
        (A) LENGTH: 66 amino acids
        (B) TYPE: amino acid
        (D) TOPOLOGY: linear
```

(xi) SEQUENCE DESCRIPTION: SEQ ID NO: 12:

```
Cys Ala Val Cys Asn Asp Tyr Ala Ser Gly Tyr His Tyr Gly Val Trp
1               5                   10                  15

Ser Cys Glu Gly Cys Lys Ala Phe Phe Lys Arg Ser Ile Gln Gly His
            20                  25                  30

Asn Asp Tyr Met Cys Pro Ala Thr Asn Gln Cys Thr Ile Asp Lys Asn
            35                  40                  45

Arg Arg Lys Ser Cys Gln Ala Cys Arg Leu Arg Lys Cys Tyr Glu Val
        50                  55                  60

Gly Met
65
```

(2) INFORMATION FOR SEQ ID NO: 13:

(i) SEQUENCE CHARACTERISTICS:
        (A) LENGTH: 484 amino acids
        (B) TYPE: amino acid
        (D) TOPOLOGY: linear (vi) ORIGINAL SOURCE:
        (A) ORGANISM: Rattus rattus (xi) SEQUENCE DESCRIPTION: SEQ ID NO: 13:

```
Met Thr Phe Tyr Ser Pro Ala Val Met Asn Tyr Ser Val Pro Gly Ser
1               5                   10                  15

Thr Ser Asn Leu Asp Gly Gly Pro Val Arg Leu Ser Thr Ser Pro Asn
            20                  25                  30

Val Leu Trp Pro Thr Ser Gly His Leu Ser Pro Leu Ala Thr His Cys
            35                  40                  45

Gln Ser Ser Leu Leu Tyr Ala Glu Pro Gln Lys Ser Pro Trp Cys Glu
        50                  55                  60

Ala Arg Ser Leu Glu His Thr Leu Pro Val Asn Arg Glu Thr Leu Lys
65                  70                  75                  80

Arg Lys Leu Ser Gly Ser Ser Cys Ala Ser Pro Val Thr Ser Pro Asn
            85                  90                  95

Ala Lys Arg Asp Ala His Phe Cys Pro Val Cys Ser Asp Tyr Ala Ser
            100                 105                 110

Gly Tyr His Tyr Gly Val Trp Ser Cys Glu Gly Cys Lys Ala Phe Phe
            115                 120                 125

Lys Arg Ser Ile Gln Gly His Asn Asp Tyr Ile Cys Pro Ala Thr Asn
    130                 135                 140

Gln Cys Thr Ile Asp Lys Asn Arg Arg Lys Ser Cys Gln Ala Cys Arg
145                 150                 155                 160

Leu Arg Lys Cys Tyr Glu Val Gly Met Val Lys Cys Gly Ser Arg Arg
                165                 170                 175

Glu Arg Cys Gly Tyr Arg Ile Val Arg Arg Gln Arg Ser Ser Ser Glu
            180                 185                 190

Gln Val His Cys Leu Ser Lys Ala Lys Arg Asn Gly Gly His Ala Pro
        195                 200                 205

Arg Val Lys Glu Leu Leu Leu Ser Thr Leu Ser Pro Glu Gln Leu Val
    210                 215                 220

Leu Thr Leu Leu Glu Ala Glu Pro Pro Asn Val Leu Val Ser Arg Pro
225                 230                 235                 240

Ser Met Pro Phe Thr Glu Ala Ser Met Met Met Ser Leu Thr Lys Leu
                245                 250                 255
```

```
Ala Asp Lys Glu Leu Val His Met Ile Gly Trp Ala Lys Lys Ile Pro
            260                 265                 270

Gly Phe Val Glu Leu Ser Leu Leu Asp Gln Val Arg Leu Leu Glu Ser
            275                 280                 285

Cys Trp Met Glu Val Leu Met Val Gly Leu Met Trp Arg Ser Ile Asp
            290                 295                 300

His Pro Gly Lys Leu Ile Phe Ala Pro Asp Leu Val Leu Asp Arg Asp
305                 310                 315                 320

Glu Gly Lys Cys Val Glu Gly Ile Leu Glu Ile Phe Asp Met Leu Leu
            325                 330                 335

Ala Thr Thr Ser Arg Phe Arg Glu Leu Lys Leu Gln His Lys Glu Tyr
            340                 345                 350

Leu Cys Val Lys Ala Met Ile Leu Leu Asn Ser Ser Met Tyr Pro Leu
            355                 360                 365

Ala Ser Ala Asn Gln Glu Ala Glu Ser Ser Arg Lys Leu Thr His Leu
            370                 375                 380

Leu Asn Ala Val Thr Asp Ala Leu Val Trp Val Ile Ala Lys Ser Gly
385                 390                 395                 400

Ile Ser Ser Gln Gln Gln Ser Val Arg Leu Ala Asn Leu Leu Met Leu
            405                 410                 415

Leu Ser His Val Arg His Ile Ser Asn Lys Gly Met Glu His Leu Leu
            420                 425                 430

Ser Met Lys Cys Lys Asn Val Val Pro Val Tyr Asp Leu Leu Leu Glu
            435                 440                 445

Met Leu Asn Ala His Thr Leu Arg Gly Tyr Lys Ser Ser Ile Ser Gly
            450                 455                 460

Ser Glu Cys Ser Ser Thr Glu Asp Ser Lys Asn Lys Glu Ser Ser Gln
465                 470                 475                 480

Asn Leu Gln Ser (2) INFORMATION FOR SEQ ID NO: 14:

(i) SEQUENCE CHARACTERISTICS:
        (A) LENGTH: 484 amino acids
        (B) TYPE: amino acid
        (D) TOPOLOGY: linear (vi) ORIGINAL SOURCE:
        (A) ORGANISM: Mus musculus (xi) SEQUENCE DESCRIPTION: SEQ ID NO: 14:

Met Ala Phe Tyr Ser Pro Ala Val Met Asn Tyr Ser Val Pro Ser Ser
1               5                   10                  15

Thr Gly Asn Leu Glu Gly Gly Pro Val Arg Gln Thr Ala Ser Pro Asn
            20                  25                  30

Val Leu Trp Pro Thr Ser Gly His Leu Ser Pro Leu Ala Thr His Cys
            35                  40                  45

Gln Ser Ser Leu Leu Tyr Ala Glu Pro Gln Lys Ser Pro Trp Cys Glu
            50                  55                  60

Ala Arg Ser Leu Glu His Thr Leu Pro Val Asn Arg Glu Thr Leu Lys
65                  70                  75                  80

Arg Lys Leu Gly Gly Ser Gly Cys Ala Ser Pro Val Thr Ser Pro Ser
            85                  90                  95

Thr Lys Arg Asp Ala His Phe Cys Ala Val Cys Ser Asp Tyr Ala Ser
            100                 105                 110

Gly Tyr His Tyr Gly Val Trp Ser Cys Glu Gly Cys Lys Ala Phe Phe
```

```
                115                 120                 125
Lys Arg Ser Ile Gln Gly His Asn Asp Tyr Ile Cys Pro Ala Thr Asn
130                 135                 140

Gln Cys Thr Ile Asp Lys Asn Arg Arg Lys Asn Cys Gln Ala Cys Arg
145                 150                 155                 160

Leu Arg Lys Cys Tyr Glu Val Gly Met Val Lys Cys Gly Ser Arg Arg
                165                 170                 175

Glu Arg Cys Gly Tyr Arg Ile Val Arg Arg Gln Arg Ser Ala Ser Glu
                180                 185                 190

Gln Val His Cys Leu Asn Lys Ala Lys Arg Thr Ser Gly His Thr Pro
                195                 200                 205

Arg Val Lys Glu Leu Leu Leu Asn Ser Leu Ser Pro Glu Gln Leu Val
210                 215                 220

Leu Thr Leu Leu Glu Ala Glu Pro Pro Asn Val Leu Val Ser Arg Pro
225                 230                 235                 240

Ser Met Pro Phe Thr Glu Ala Ser Met Met Met Ser Leu Thr Lys Leu
                245                 250                 255

Ala Asp Lys Glu Leu Val His Met Ile Gly Trp Ala Lys Lys Ile Pro
                260                 265                 270

Gly Phe Val Glu Leu Ser Leu Leu Asp Gln Val Arg Leu Leu Glu Ser
                275                 280                 285

Cys Trp Met Glu Val Leu Met Val Gly Leu Met Trp Arg Ser Ile Asp
290                 295                 300

His Pro Gly Lys Leu Ile Phe Ala Pro Asp Leu Val Leu Asp Arg Asp
305                 310                 315                 320

Glu Gly Lys Cys Val Glu Gly Ile Leu Glu Ile Phe Asp Met Leu Leu
                325                 330                 335

Ala Thr Thr Ala Arg Phe Arg Glu Leu Lys Leu Gln His Lys Glu Tyr
                340                 345                 350

Leu Cys Val Lys Ala Met Ile Leu Leu Asn Ser Ser Met Tyr His Leu
                355                 360                 365

Ala Thr Ala Ser Gln Glu Ala Glu Ser Ser Arg Lys Leu Thr His Leu
                370                 375                 380

Leu Asn Ala Val Thr Asp Ala Leu Val Trp Val Ile Ser Lys Ser Arg
385                 390                 395                 400

Ile Ser Ser Gln Gln Gln Ser Val Arg Leu Ala Asn Leu Leu Met Leu
                405                 410                 415

Leu Ser His Val Arg His Ile Ser Asn Lys Gly Met Glu His Leu Leu
                420                 425                 430

Ser Met Lys Cys Lys Asn Val Val Pro Val Tyr Asp Leu Leu Leu Glu
                435                 440                 445

Met Leu Asn Ala His Thr Leu Arg Gly Tyr Lys Ser Ser Ile Ser Gly
                450                 455                 460

Ser Gly Cys Cys Ser Thr Glu Asp Ser Lys Ser Lys Glu Gly Ser Gln
465                 470                 475                 480

Asn Leu Gln Ser (2) INFORMATION FOR SEQ ID NO: 15:

(i) SEQUENCE CHARACTERISTICS:
        (A) LENGTH: 384 amino acids
        (B) TYPE: amino acid
        (D) TOPOLOGY: linear (vi) ORIGINAL SOURCE:
```

(A) ORGANISM: Homo sapiens (xi) SEQUENCE DESCRIPTION: SEQ ID NO: 15:

```
Ala Leu Ser Pro Leu Val Val His Arg Gln Leu Ser His Leu Tyr Ala
1               5                   10                  15

Glu Pro Gln Lys Ser Pro Trp Cys Glu Ala Arg Ser Leu Glu His Thr
            20                  25                  30

Leu Pro Val Asn Arg Glu Thr Leu Lys Arg Lys Val Ser Gly Asn Arg
            35                  40                  45

Cys Ala Ser Pro Val Thr Gly Pro Gly Ser Lys Arg Asp Ala His Phe
50                  55                  60

Cys Ala Val Cys Ser Asp Tyr Ala Ser Gly Tyr His Tyr Gly Val Trp
65                  70                  75                  80

Ser Cys Glu Gly Cys Lys Ala Phe Phe Lys Arg Ser Ile Gln Gly His
                85                  90                  95

Asn Asp Tyr Ile Cys Pro Ala Thr Asn Gln Cys Thr Ile Asp Lys Asn
            100                 105                 110

Arg Arg Lys Ser Cys Gln Ala Cys Arg Leu Arg Lys Cys Tyr Glu Val
            115                 120                 125

Gly Met Val Lys Cys Gly Ser Arg Arg Glu Arg Cys Gly Tyr Arg Leu
    130                 135                 140

Val Arg Arg Gln Arg Ser Ala Asp Glu Gln Leu His Cys Ala Gly Lys
145                 150                 155                 160

Ala Lys Arg Ser Gly Gly His Ala Pro Arg Val Arg Glu Leu Leu Leu
                165                 170                 175

Asp Ala Leu Ser Pro Glu Gln Leu Val Leu Thr Leu Leu Glu Ala Glu
            180                 185                 190

Pro Pro His Val Leu Ile Ser Arg Pro Ser Ala Pro Phe Thr Glu Ala
        195                 200                 205

Ser Met Met Met Ser Leu Thr Lys Leu Ala Asp Lys Glu Leu Val His
    210                 215                 220

Met Ile Ser Trp Ala Lys Lys Ile Pro Gly Phe Val Glu Leu Ser Leu
225                 230                 235                 240

Phe Asp Gln Val Arg Leu Leu Glu Ser Cys Trp Met Glu Val Leu Met
                245                 250                 255

Met Gly Leu Met Trp Arg Ser Ile Asp His Pro Gly Lys Leu Ile Phe
            260                 265                 270

Ala Pro Asp Leu Val Leu Asp Arg Asp Glu Gly Lys Cys Val Glu Gly
            275                 280                 285

Ile Leu Glu Ile Phe Asp Met Leu Leu Ala Thr Thr Ser Arg Phe Arg
290                 295                 300

Glu Leu Lys Leu Gln His Lys Glu Tyr Leu Cys Val Lys Ala Met Ile
305                 310                 315                 320

Leu Leu Asn Ser Ser Met Tyr Pro Leu Val Thr Ala Thr Gln Asp Ala
                325                 330                 335

Asp Ser Ser Arg Lys Leu Ala His Leu Leu Asn Ala Val Thr Asp Ala
            340                 345                 350

Leu Val Trp Val Ile Ala Lys Ser Gly Ile Ser Ser Gln Gln Gln Ser
        355                 360                 365

Met Arg Leu Ala Asn Leu Leu Met Leu Leu Ser His Val Arg His Ala
370                 375                 380
```

(2) INFORMATION FOR SEQ ID NO: 16:

(i) SEQUENCE CHARACTERISTICS:
    (A) LENGTH: 596 amino acids
    (B) TYPE: amino acid
    (D) TOPOLOGY: linear (vi) ORIGINAL SOURCE:
    (A) ORGANISM: Rattus rattus (xi) SEQUENCE DESCRIPTION: SEQ ID NO: 16:

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Met Pro Met Glu Arg Ala Leu Gly Glu Val Tyr Val Asp Asn Ser Lys
        35                  40                  45

Pro Ala Val Phe Asn Tyr Pro Glu Gly Ala Ala Tyr Glu Phe Asn Ala
    50                  55                  60

Ala Ala Ala Ala Ala Ala Gly Ala Ser Ala Pro Val Tyr Gly Gln
65                  70                  75                  80

Ser Ser Ile Thr Tyr Gly Pro Gly Ser Glu Ala Ala Phe Gly Ala
                85                  90                  95

Asn Ser Leu Gly Ala Phe Pro Gln Leu Asn Ser Val Ser Pro Ser Pro
            100                 105                 110

Ile Met Ile Leu His Pro Pro His Val Ser Pro Phe Leu His Pro
                115                 120                 125

His Gly His Gln Val Pro Tyr Tyr Leu Glu Asn Glu Pro Ser Ala Tyr
    130                 135                 140

Ala Val Arg Asp Thr Gly Pro Pro Ala Phe Tyr Arg Ser Asn Ser Asp
145                 150                 155                 160

Asn Arg Arg Gln Asn Gly Arg Glu Arg Leu Ser Ser Ser Ser Glu Lys
                165                 170                 175

Gly Asn Met Ile Met Glu Ser Ala Lys Glu Thr Arg Tyr Cys Ala Val
            180                 185                 190

Cys Asn Asp Tyr Ala Ser Gly Tyr His Tyr Gly Val Trp Ser Cys Glu
        195                 200                 205

Gly Cys Lys Ala Phe Phe Lys Arg Ser Ile Gln Gly His Asn Asp Tyr
    210                 215                 220

Met Cys Pro Ala Thr Asn Gln Cys Thr Ile Asp Lys Asn Arg Arg Lys
225                 230                 235                 240

Ser Cys Gln Ala Cys Arg Leu Arg Lys Cys Tyr Glu Val Gly Met Met
                245                 250                 255

Lys Gly Gly Ile Arg Lys Asp Arg Arg Gly Gly Arg Met Leu Lys His
            260                 265                 270

Lys Arg Gln Arg Asp Asp Leu Glu Gly Arg Asn Glu Met Gly Thr Ser
        275                 280                 285

Gly Asp Met Arg Ala Ala Asn Leu Trp Pro Ser Pro Leu Val Ile Lys
    290                 295                 300

His Thr Lys Lys Asn Ser Pro Ala Leu Ser Leu Thr Ala Asp Gln Met
305                 310                 315                 320

Val Ser Ala Leu Leu Asp Ala Glu Pro Pro Leu Ile Tyr Ser Glu Tyr
                325                 330                 335

Asp Pro Ser Arg Pro Phe Ser Glu Ala Ser Met Met Gly Leu Leu Thr
            340                 345                 350

Asn Leu Ala Asp Arg Glu Leu Val His Met Ile Asn Trp Ala Lys Arg
        355                 360                 365
```

```
Val Pro Gly Phe Gly Asp Leu Asn Leu His Asp Gln Val His Leu Leu
    370             375                 380
Glu Cys Ala Trp Leu Glu Ile Leu Met Ile Gly Leu Val Trp Arg Ser
385                 390                 395                 400
Met Glu His Pro Gly Lys Leu Leu Phe Ala Pro Asn Leu Leu Leu Asp
                405                 410                 415
Arg Asn Gln Gly Lys Cys Val Glu Gly Met Val Glu Ile Phe Asp Met
            420                 425                 430
Leu Leu Ala Thr Ser Ser Arg Phe Arg Met Met Asn Leu Gln Gly Glu
        435                 440                 445
Glu Phe Val Cys Leu Lys Ser Ile Ile Leu Leu Asn Ser Gly Val Tyr
    450                 455                 460
Thr Phe Leu Ser Ser Thr Leu Lys Ser Leu Glu Glu Lys Asp His Ile
465                 470                 475                 480
His Arg Val Leu Asp Lys Ile Asn Asp Thr Leu Ile His Leu Met Ala
                485                 490                 495
Lys Ala Gly Leu Thr Leu Gln Gln Gln His Arg Arg Leu Ala Gln Leu
            500                 505                 510
Leu Leu Ile Leu Ser His Ile Arg His Met Ser Asn Lys Gly Met Glu
        515                 520                 525
His Leu Tyr Asn Met Lys Cys Lys Asn Val Val Pro Leu Tyr Asp Leu
    530                 535                 540
Leu Leu Glu Met Leu Asp Ala His Arg Leu His Ala Pro Ala Ser Arg
545                 550                 555                 560
Met Gly Val Pro Pro Glu Glu Pro Ser Gln Ser Gln Leu Thr Thr Thr
                565                 570                 575
Ser Ser Thr Ser Ala His Ser Leu Gln Thr Tyr Tyr Ile Pro Pro Glu
            580                 585                 590
Ala Glu Gly Phe
        595

(2) INFORMATION FOR SEQ ID NO: 17:

(i) SEQUENCE CHARACTERISTICS:
        (A) LENGTH: 591 amino acids
        (B) TYPE: amino acid
        (D) TOPOLOGY: linear (vi) ORIGINAL SOURCE:
        (A) ORGANISM: Homo sapiens (xi) SEQUENCE DESCRIPTION: SEQ ID NO: 17:

Met Thr Met Thr Leu His Thr Lys Ala Ser Gly Met Ala Leu Leu His
1               5                   10                  15
Gln Ile Gln Gly Asn Glu Leu Glu Pro Leu Asn Arg Pro Gln Leu Lys
            20                  25                  30
Ile Pro Leu Glu Arg Pro Leu Gly Glu Val Tyr Leu Asp Ser Ser Lys
        35                  40                  45
Pro Ala Val Tyr Asn Tyr Pro Glu Gly Ala Ala Tyr Glu Phe Asn Ala
    50                  55                  60
Ala Ala Ala Ala Asn Ala Gln Val Tyr Gly Gln Thr Gly Leu Pro Tyr
65                  70                  75                  80
Gly Pro Gly Ser Glu Ala Ala Ala Phe Gly Ser Asn Gly Leu Gly Gly
                85                  90                  95
Phe Pro Pro Leu Asn Ser Val Ser Pro Ser Pro Ile Met Ile Leu His
            100                 105                 110
```

```
Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
```

-continued

```
        530                 535                 540
Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe
            580                 585                 590
```

(2) INFORMATION FOR SEQ ID NO: 18:

(i) SEQUENCE CHARACTERISTICS:
        (A) LENGTH: 518 amino acids
        (B) TYPE: amino acid
        (D) TOPOLOGY: linear (vi) ORIGINAL SOURCE:
        (A) ORGANISM: Homo sapiens (xi) SEQUENCE DESCRIPTION: SEQ ID NO: 18:

```
Met Gly Leu Glu Met Ser Ser Lys Asp Ser Pro Gly Ser Leu Asp Gly
1               5                   10                  15

Arg Ala Trp Glu Asp Ala Gln Lys Pro Gln Ser Ala Trp Cys Gly Gly
                20                  25                  30

Arg Lys Thr Arg Val Tyr Ala Thr Ser Ser Arg Arg Ala Pro Pro Ser
            35                  40                  45

Glu Gly Thr Arg Arg Gly Gly Ala Ala Arg Pro Glu Glu Ala Ala Glu
        50                  55                  60

Glu Gly Pro Pro Ala Ala Pro Gly Ser Leu Arg His Ser Gly Pro Leu
65                  70                  75                  80

Gly Pro His Ala Cys Pro Thr Ala Leu Pro Glu Pro Gln Val Thr Ser
                85                  90                  95

Ala Met Ser Ser Gln Val Val Gly Ile Glu Pro Leu Tyr Ile Lys Ala
                100                 105                 110

Glu Pro Ala Ser Pro Asp Ser Pro Lys Gly Ser Ser Glu Thr Glu Thr
            115                 120                 125

Glu Pro Pro Val Ala Leu Ala Pro Gly Pro Ala Pro Thr Arg Cys Leu
        130                 135                 140

Pro Gly His Lys Glu Glu Glu Asp Gly Glu Gly Ala Gly Pro Gly Glu
145                 150                 155                 160

Gln Gly Gly Gly Lys Leu Val Leu Ser Ser Leu Pro Lys Arg Leu Cys
                165                 170                 175

Leu Val Cys Gly Asp Val Ala Ser Gly Tyr His Tyr Gly Val Ala Ser
                180                 185                 190

Cys Glu Ala Cys Lys Ala Phe Phe Lys Arg Thr Ile Gln Gly Ser Ile
            195                 200                 205

Glu Tyr Ser Cys Pro Ala Ser Asn Glu Cys Glu Ile Thr Lys Arg Arg
        210                 215                 220

Arg Lys Ala Cys Gln Ala Cys Arg Phe Thr Lys Cys Ile Arg Val Gly
225                 230                 235                 240

Met Leu Lys Glu Gly Val Arg Leu Asp Arg Val Arg Gly Gly Arg Gln
                245                 250                 255

Lys Tyr Lys Arg Arg Pro Glu Val Asp Pro Leu Pro Phe Pro Gly Pro
            260                 265                 270

Phe Pro Ala Gly Pro Leu Ala Val Ala Gly Gly Pro Arg Lys Thr Ala
        275                 280                 285

Ala Pro Val Asn Ala Leu Val Ser His Leu Leu Val Val Glu Pro Glu
```

-continued

```
                290                 295                 300
Lys Leu Tyr Ala Met Pro Asp Pro Ala Gly Pro Asp Gly His Leu Pro
305                 310                 315                 320

Ala Val Ala Thr Leu Cys Asp Leu Phe Asp Arg Glu Ile Val Val Thr
                325                 330                 335

Ile Ser Trp Ala Lys Ser Ile Pro Gly Phe Ser Ser Leu Ser Leu Ser
                340                 345                 350

Asp Gln Met Ser Val Leu Gln Ser Val Trp Met Glu Val Leu Val Leu
                355                 360                 365

Gly Val Ala Gln Arg Ser Leu Pro Leu Gln Asp Glu Leu Ala Phe Ala
    370                 375                 380

Glu Asp Leu Val Leu Ile Glu Glu Gly Ala Arg Ala Ala Gly Leu Gly
385                 390                 395                 400

Glu Leu Gly Ala Ala Leu Leu Gln Leu Val Arg Arg Leu Gln Ala Leu
                405                 410                 415

Arg Leu Glu Arg Glu Glu Tyr Val Leu Leu Lys Ala Leu Ala Leu Ala
                420                 425                 430

Asn Ser Asp Ser Val His Ile Glu Asp Glu Pro Arg Leu Trp Ser Ser
                435                 440                 445

Cys Glu Lys Leu Leu His Glu Ala Leu Leu Glu Tyr Glu Ala Gly Arg
    450                 455                 460

Ala Gly Pro Gly Gly Gly Ala Glu Arg Arg Arg Ala Gly Arg Leu Leu
465                 470                 475                 480

Leu Thr Leu Pro Leu Leu Arg Gln Thr Ala Gly Lys Val Leu Ala His
                485                 490                 495

Phe Tyr Gly Val Lys Leu Glu Gly Lys Val Pro Met His Lys Leu Phe
                500                 505                 510

Leu Glu Met Leu Glu Ala
            515

(2) INFORMATION FOR SEQ ID NO: 19:

(i) SEQUENCE CHARACTERISTICS:
        (A) LENGTH: 431 amino acids
        (B) TYPE: amino acid
        (D) TOPOLOGY: linear (vi) ORIGINAL SOURCE:
        (A) ORGANISM: Homo sapiens (xi) SEQUENCE DESCRIPTION: SEQ ID NO: 19:

Met Ser Ser Glu Asp Arg His Leu Gly Ser Ser Cys Gly Ser Phe Ile
1               5                   10                  15

Lys Thr Glu Pro Ser Ser Pro Ser Ser Gly Ile Asp Ala Leu Ser His
                20                  25                  30

His Ser Pro Ser Gly Ser Ser Asp Ala Ser Gly Gly Phe Gly Met Ala
            35                  40                  45

Leu Gly Thr His Ala Asn Gly Leu Asp Ser Pro Pro Met Phe Ala Gly
    50                  55                  60

Ala Gly Leu Gly Gly Asn Pro Cys Arg Lys Ser Tyr Glu Asp Cys Thr
65                  70                  75                  80

Ser Gly Ile Met Glu Asp Ser Ala Ile Lys Cys Glu Tyr Met Leu Asn
                85                  90                  95

Ala Ile Pro Lys Arg Leu Cys Leu Val Cys Gly Asp Ile Ala Ser Gly
                100                 105                 110

Tyr His Tyr Gly Val Ala Ser Cys Glu Ala Cys Lys Ala Phe Phe Lys
```

-continued

```
            115                 120                 125
Arg Thr Ile Gln Gly Asn Ile Glu Tyr Ser Cys Pro Ala Thr Asn Glu
        130                 135                 140

Cys Glu Ile Thr Lys Arg Arg Arg Lys Ser Cys Gln Ala Cys Arg Phe
145                 150                 155                 160

Met Lys Cys Ile Lys Val Gly Met Leu Lys Glu Gly Val Arg Leu Asp
                165                 170                 175

Arg Val Arg Gly Gly Arg Gln Lys Tyr Lys Arg Arg Leu Asp Ser Glu
                180                 185                 190

Asn Ser Pro Tyr Leu Ser Leu Gln Ile Ser Pro Pro Ala Lys Lys Pro
            195                 200                 205

Leu Thr Lys Ile Val Ser Tyr Leu Leu Val Ala Glu Pro Asp Lys Leu
        210                 215                 220

Tyr Ala Met Pro Pro Asp Asp Val Pro Glu Gly Asp Ile Lys Ala Leu
225                 230                 235                 240

Thr Thr Leu Cys Asp Leu Ala Asp Arg Glu Leu Val Phe Leu Ile Ser
                245                 250                 255

Trp Ala Lys His Ile Pro Gly Phe Ser Asn Leu Thr Leu Gly Asp Gln
                260                 265                 270

Met Ser Leu Leu Gln Ser Ala Trp Met Glu Ile Leu Ile Leu Gly Ile
            275                 280                 285

Val Tyr Arg Ser Leu Pro Tyr Asp Asp Lys Leu Ala Tyr Ala Glu Asp
        290                 295                 300

Tyr Ile Met Asp Glu Glu His Ser Arg Leu Val Gly Leu Leu Glu Leu
305                 310                 315                 320

Tyr Arg Ala Ile Leu Gln Leu Val Arg Arg Tyr Lys Lys Leu Lys Val
                325                 330                 335

Glu Lys Glu Glu Phe Val Met Leu Lys Ala Ile Ala Leu Ala Asn Ser
                340                 345                 350

Asp Ser Met Tyr Ile Glu Asn Leu Glu Ala Val Gln Lys Leu Gln Asp
            355                 360                 365

Leu Leu His Glu Ala Leu Gln Asp Tyr Glu Leu Ser Gln Arg His Glu
        370                 375                 380

Glu Pro Arg Arg Ala Gly Lys Leu Leu Leu Thr Leu Pro Leu Leu Arg
385                 390                 395                 400

Gln Thr Ala Ala Lys Ala Val Gln His Phe Tyr Ser Val Lys Leu Gln
                405                 410                 415

Gly Lys Val Pro Met His Lys Leu Phe Leu Glu Met Leu Glu Ala
                420                 425                 430
```